(12) United States Patent
O'Halloran et al.

(10) Patent No.: US 10,595,884 B2
(45) Date of Patent: Mar. 24, 2020

(54) METHODS AND APPARATUS FOR TREATING VERTEBRAL FRACTURES

(71) Applicant: GLOBUS MEDICAL, INC., Audubon, PA (US)

(72) Inventors: Damien O'Halloran, Conshohocken, PA (US); Sean Suh, Morganville, NJ (US); Daniel Waite, Pottstown, PA (US)

(73) Assignee: Globus Medical, Inc., Audubon, PA (US)

( * ) Notice: Subject to any disclaimer, the term of this patent is extended or adjusted under 35 U.S.C. 154(b) by 763 days.

(21) Appl. No.: 15/051,000

(22) Filed: Feb. 23, 2016

(65) Prior Publication Data
US 2016/0166262 A1    Jun. 16, 2016

Related U.S. Application Data

(63) Continuation of application No. 12/823,622, filed on Jun. 25, 2010, now Pat. No. 9,295,509, which is a continuation of application No. 12/708,233, filed on Feb. 18, 2010, now Pat. No. 9,220,554.

(51) Int. Cl.
| | |
|---|---|
| *A61B 17/16* | (2006.01) |
| *A61B 17/70* | (2006.01) |
| *A61B 17/88* | (2006.01) |
| *A61B 17/12* | (2006.01) |
| *A61B 17/34* | (2006.01) |

(52) U.S. Cl.
CPC .... *A61B 17/1671* (2013.01); *A61B 17/12136* (2013.01); *A61B 17/7097* (2013.01); *A61B 17/8852* (2013.01); *A61B 17/8855* (2013.01); *A61B 17/3472* (2013.01); *A61B 2017/3445* (2013.01); *A61B 2017/3454* (2013.01)

(58) Field of Classification Search
CPC .................................................. A61B 17/1671
See application file for complete search history.

(56) References Cited

U.S. PATENT DOCUMENTS

| | | | | |
|---|---|---|---|---|
| 2,655,154 A | * | 10/1953 | Richter | A61B 17/320016 30/152 |
| 5,113,846 A | * | 5/1992 | Hiltebrandt | A61B 1/32 600/225 |
| 6,676,665 B2 | * | 1/2004 | Foley | A61B 17/025 600/201 |
| 7,114,501 B2 | * | 10/2006 | Johnson | A61B 17/320016 128/877 |
| 2001/0034526 A1 | * | 10/2001 | Kuslich | A61B 17/1617 606/80 |
| 2002/0022856 A1 | * | 2/2002 | Johnson | A61B 17/320016 606/185 |

(Continued)

*Primary Examiner* — Zade Coley

(57) ABSTRACT

Methods and apparatus for treating bones, including, in one or more embodiments, methods and apparatus for treatment of vertebral fractures that include a containment assembly for cement containment and/or a balloon assembly for maintaining vertebral height. Methods for treating a bone comprising: creating a cavity in the bone; inserting a containment jacket into the cavity; inserting a balloon into the containment jacket; inflating the balloon; and introducing a filler material into the containment jacket with isolation of the balloon from the filler material.

14 Claims, 31 Drawing Sheets

(56) References Cited

U.S. PATENT DOCUMENTS

| | | | | |
|---|---|---|---|---|
| 2002/0068974 | A1* | 6/2002 | Kuslich | A61B 17/68 623/17.11 |
| 2004/0215197 | A1* | 10/2004 | Smith | A61B 17/1671 606/79 |
| 2005/0113838 | A1* | 5/2005 | Phillips | A61B 17/1604 606/80 |
| 2005/0182413 | A1* | 8/2005 | Johnson | A61B 17/320016 606/79 |
| 2006/0116689 | A1* | 6/2006 | Albans | A61B 17/025 606/92 |
| 2008/0086133 | A1* | 4/2008 | Kuslich | A61B 17/1617 606/250 |
| 2008/0114364 | A1* | 5/2008 | Goldin | A61B 17/1617 606/79 |
| 2008/0300636 | A1* | 12/2008 | Carli | A61B 17/025 606/280 |
| 2010/0036381 | A1* | 2/2010 | Vanleeuwen | A61B 17/1617 606/80 |

* cited by examiner

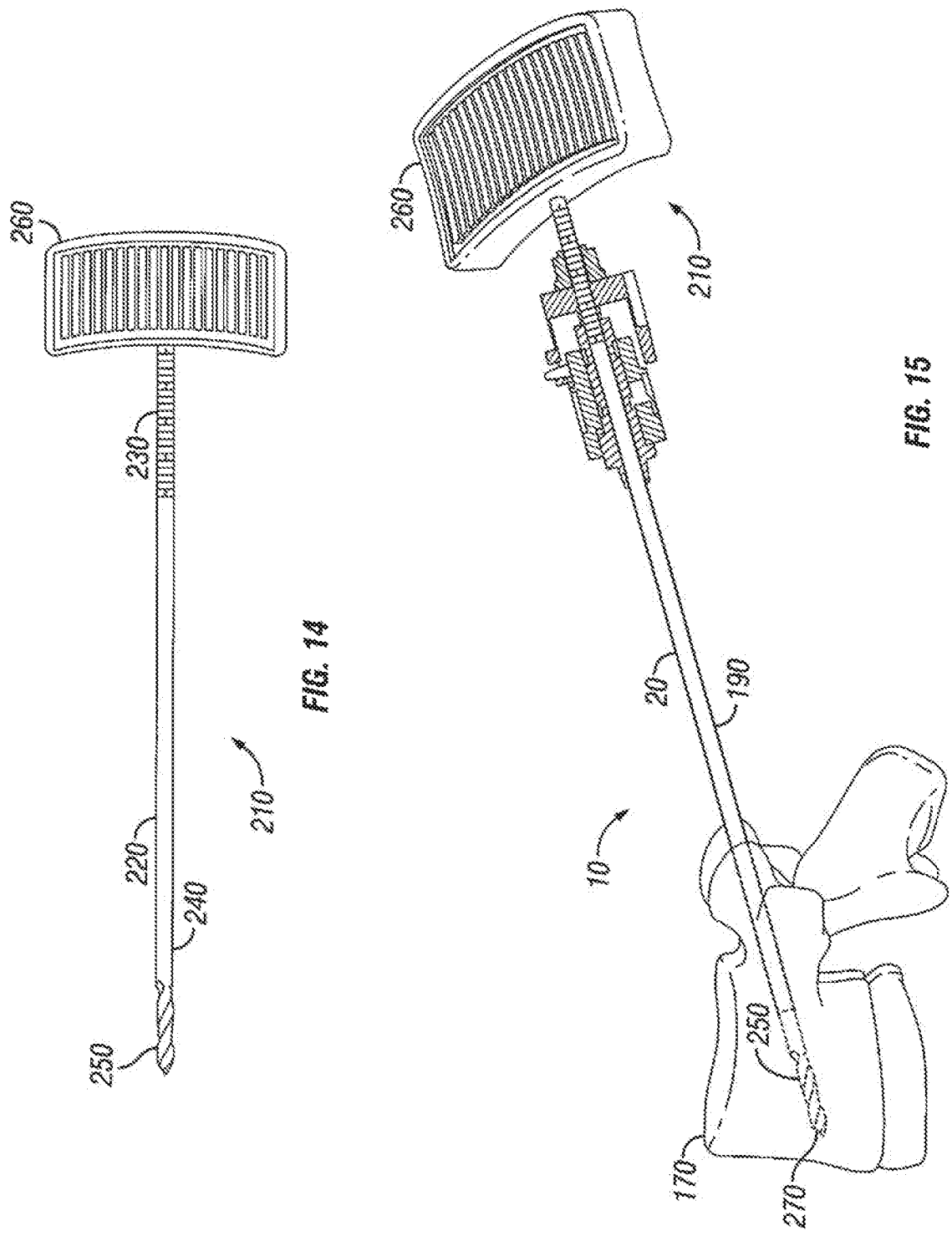

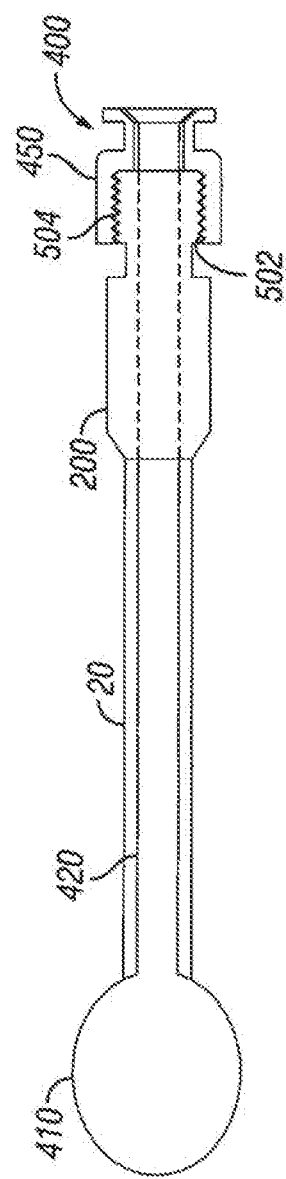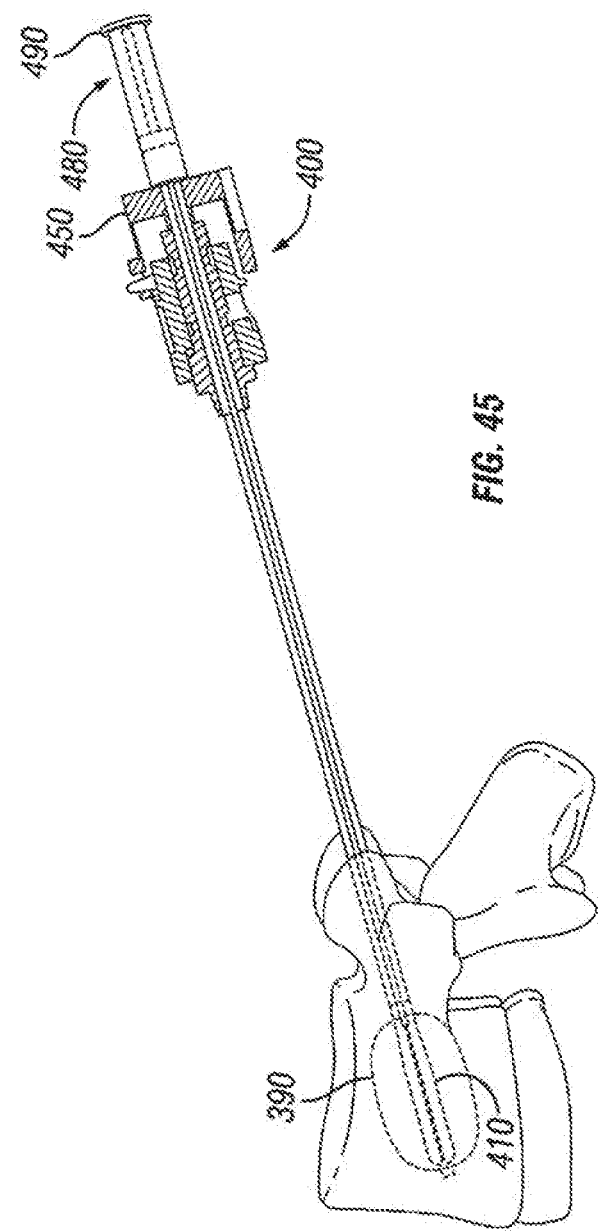

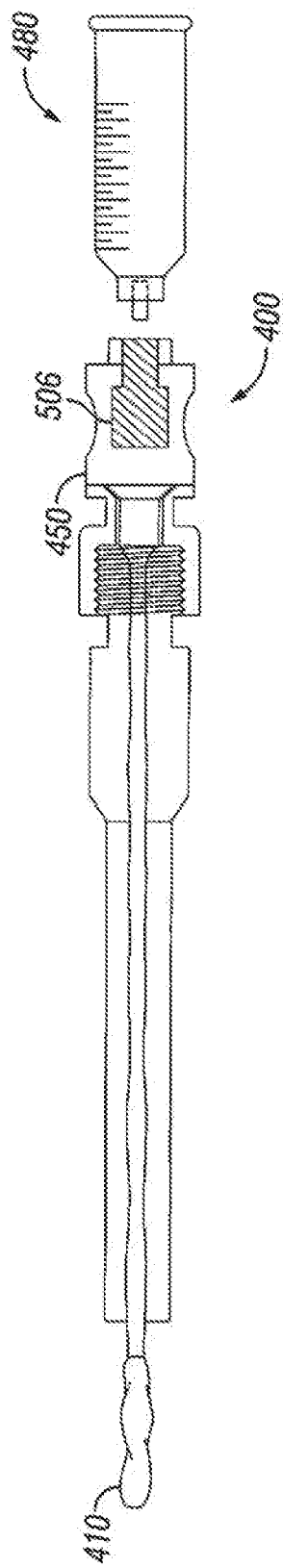
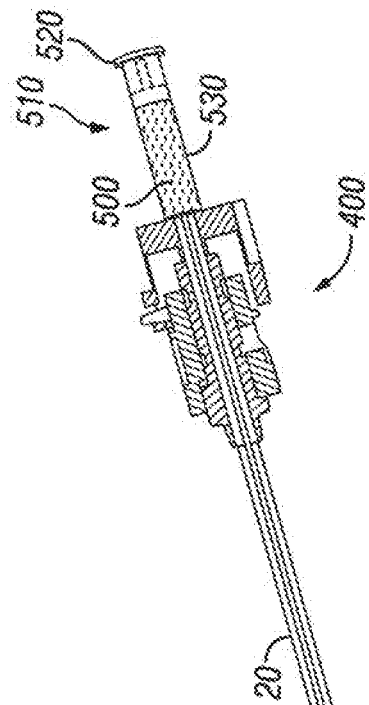
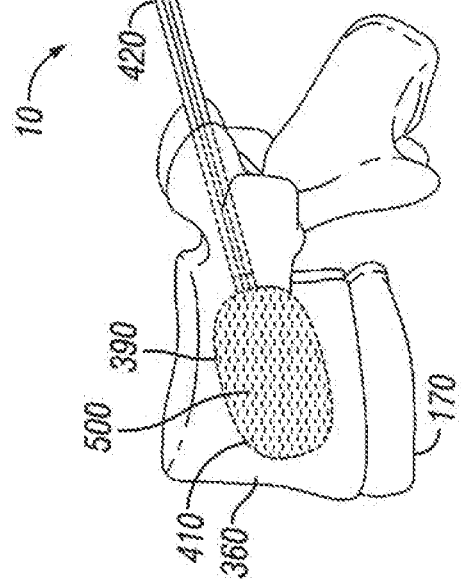
FIG. 46
FIG. 47

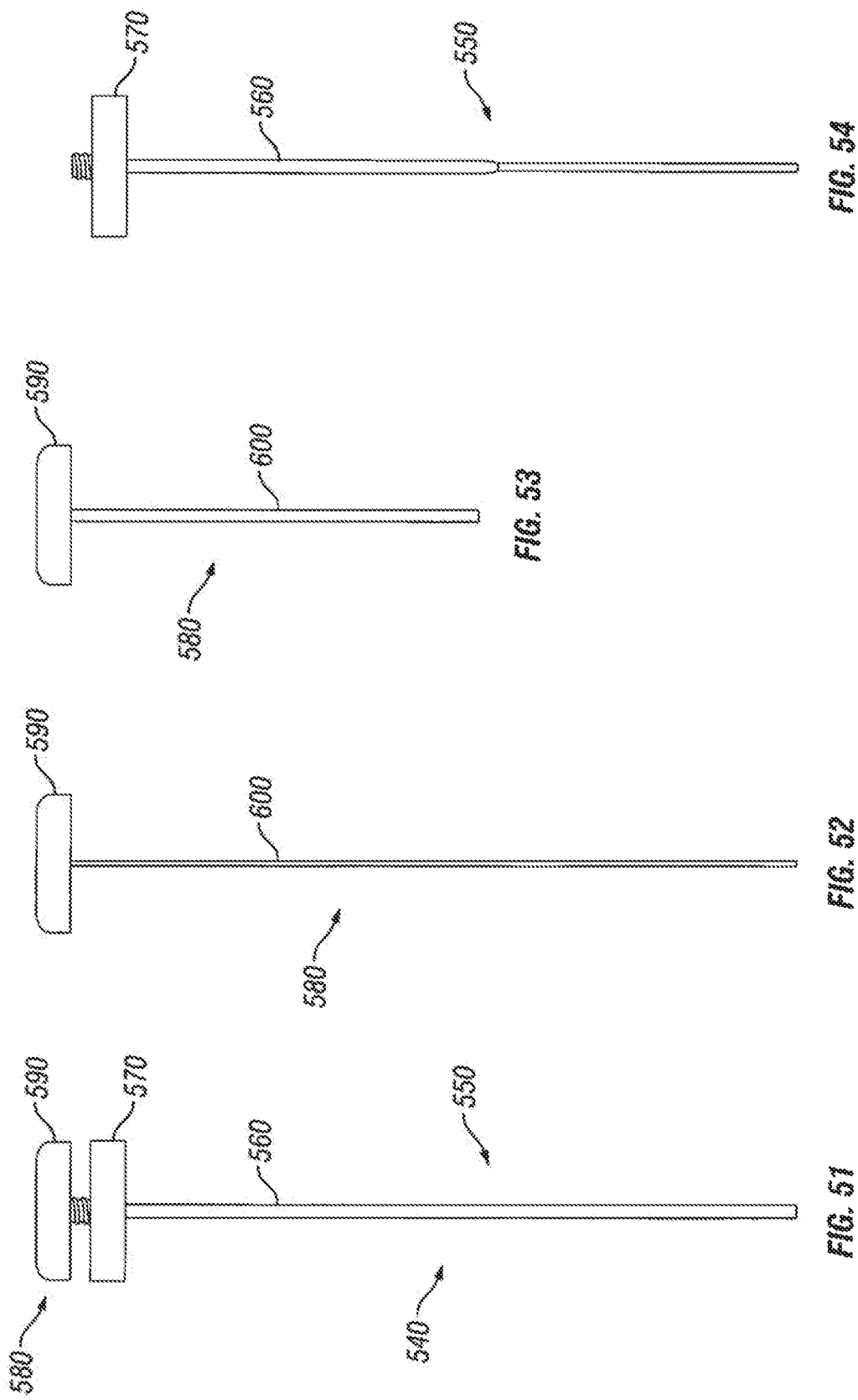

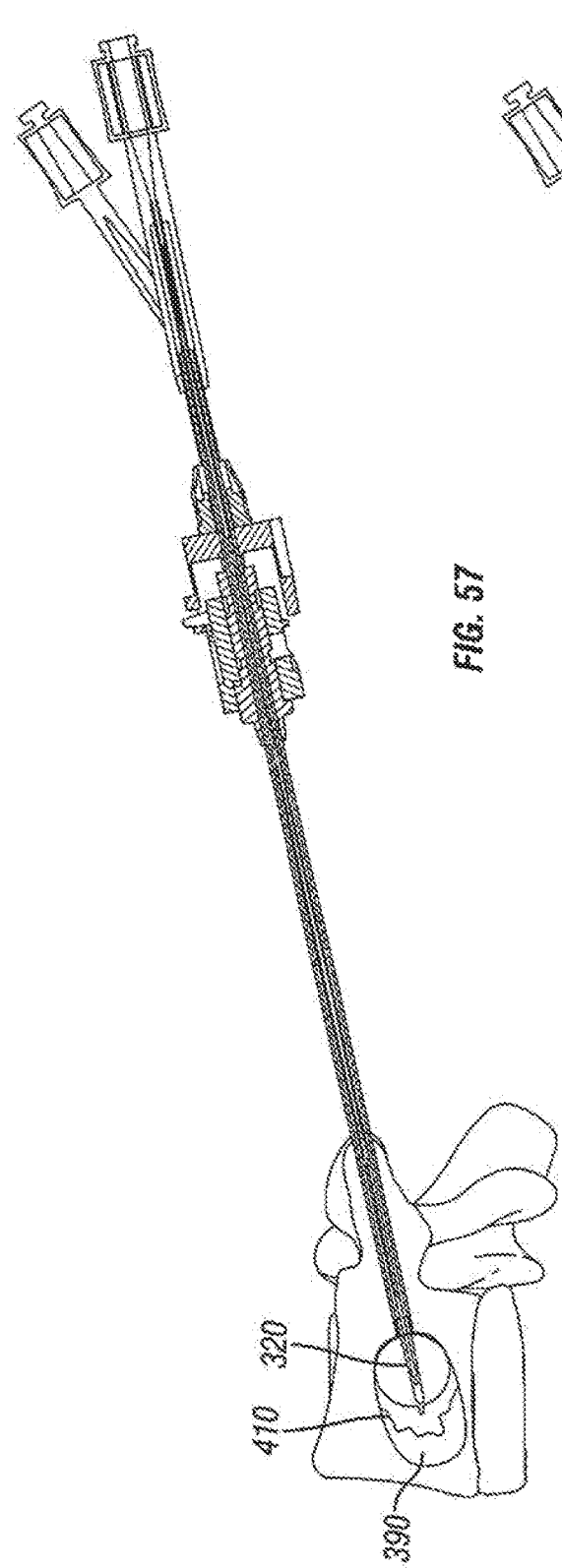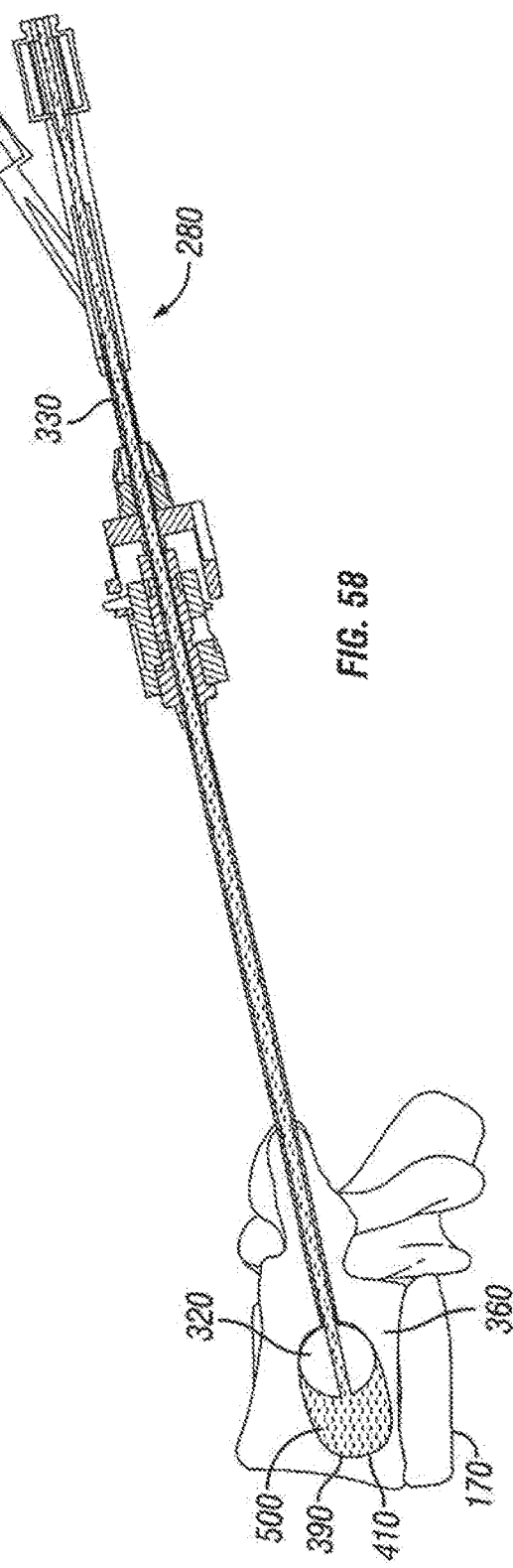

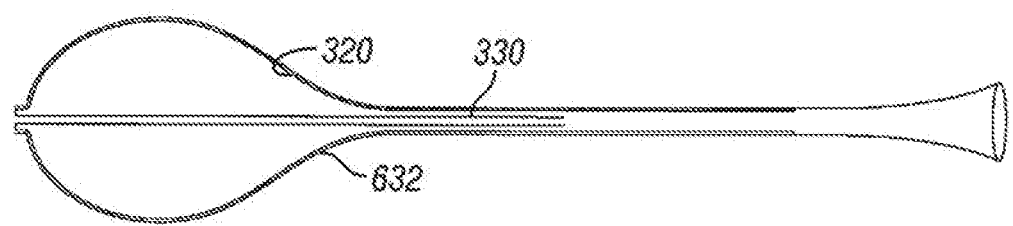
FIG. 59
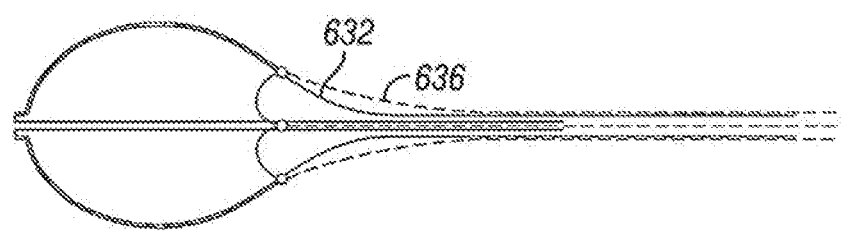
FIG. 60
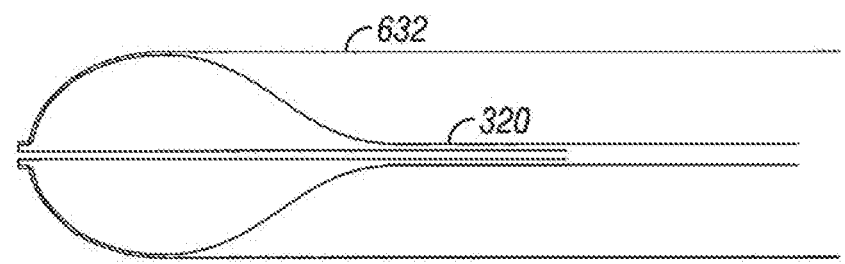
FIG. 61
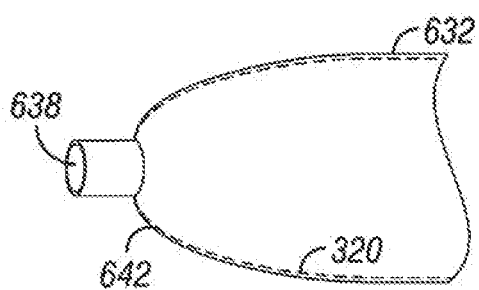 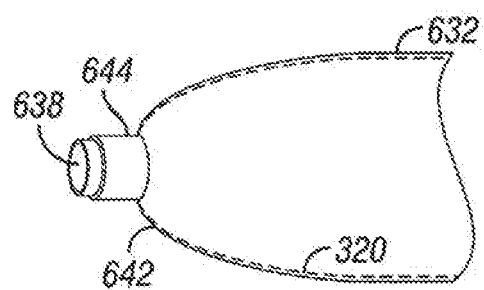
FIG. 62     FIG. 63

METHODS AND APPARATUS FOR TREATING VERTEBRAL FRACTURES

CROSS-REFERENCE TO RELATED APPLICATIONS

The present application is a continuation of U.S. patent application Ser. No. 12/823,622, filed Jun. 25, 2010, which is a continuation of U.S. patent application Ser. No. 12/708,233, filed Feb. 18, 2010, now issued as U.S. Pat. No. 9,220,554, the disclosures of which are incorporated herein by reference in their entireties.

FIELD OF THE INVENTION

The present disclosure generally relates to treatment of bones. In particular, in one or more embodiments, the present disclosure relates to methods and apparatus for treatment of vertebral fractures that include a containment assembly for cement containment and/or a balloon assembly for maintaining vertebral height.

BACKGROUND

Bones and bony structures are susceptible to a variety of weaknesses that can affect their ability to provide support and structure. Weaknesses in bony structures may have many causes, including degenerative diseases, tumors, fractures, and dislocations. By way of example, weaknesses in vertebrae can lead to compression fractures that involve the collapse of one or more vertebrae in the spine. These vertebral compression fractures may be caused by a number of conditions including osteoporosis, trauma, and tumors. Advances in medicine and engineering have provided doctors with a plurality of devices and techniques for alleviating or curing these weaknesses.

One technique for treating vertebral fractures is vertebroplasty. In vertebroplasty, a physician may use a needle to inject bone cement into a fractured vertebral body to stabilize the fracture. Kyphoplasty is another technique for treating vertebra fractures that involves insertion of a balloon into the fractured vertebra to restore the height of the vertebra. The balloon may then be removed followed by injection of bone cement into the vertebral body to stabilize the fracture. Leakage of the bone cement in both vertebroplasty and kyphoplasty is a common problem that can lead to complications. Another problem associated with these techniques is the potential for inadequate height restoration to the fractured vertebral body.

Thus, there is a need for methods and apparatus that can provide stabilization to a fractured vertebra

SUMMARY

The present disclosure generally relates to treatment of bones. In particular, in one or more embodiments, the present disclosure relates to methods and apparatus for treatment of vertebral fractures that include a containment assembly for cement containment and/or a balloon assembly for maintaining vertebral height.

An embodiment includes a method for treating a bone. The method may comprise creating a cavity in the bone. The method may further comprise inserting a containment jacket into the cavity. The method may further comprise inserting a balloon into the containment jacket. The method may further comprise inflating the balloon. The method may further comprise introducing a filler material into the containment jacket with isolation of the balloon from the filler material.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of the present invention and should not be used to limit or define the invention.

FIG. 14 illustrates a drill that can be used in accordance with one embodiment of the present invention.

FIG. 15 illustrates insertion of a drill through the cannula assembly to create a channel in a vertebral body in accordance with one embodiment of the present invention.

FIG. 44 illustrates coupling of a cannula assembly and a containment assembly with removal of the mandrel in accordance with one embodiment of the present invention.

FIGS. 45-46 illustrate removal of fluid from a containment jacket placed in a vertebral body in accordance with embodiments of the present invention.

FIG. 47 illustrates use of a syringe-type device to introduce filler material into a containment jacket placed in a vertebral body in accordance with one embodiment of the present invention.

FIGS. 50-54 illustrate needle-type devices that may be used in accordance with embodiments of the present invention.

FIG. 57 illustrates inflation of a balloon in a containment jacket placed within a vertebral body in accordance with one embodiment of the present invention.

FIG. 58 illustrates introduction of a filler material into a vertebral body while using a balloon in accordance with one embodiment of the present invention.

FIG. 59 illustrates isolation of the balloon from the filler material in accordance with one embodiment of the present invention.

FIG. 60 illustrates isolation of the balloon from the filler material in accordance with another embodiment of the present invention.

FIGS. 61-63 illustrate isolation of the balloon from the filler material in accordance with embodiments of the present invention.

DETAILED DESCRIPTION OF THE ILLUSTRATED EMBODIMENTS

Figure 1:
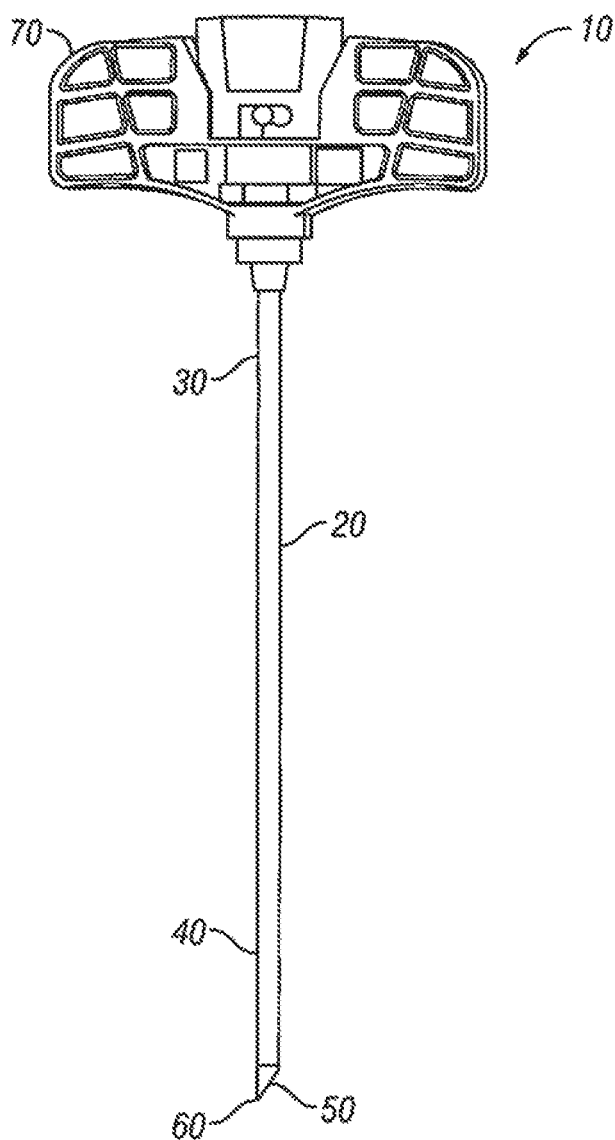
FIG. 1 illustrates a cannula assembly in accordance with one embodiment of the present technique.

Embodiments of the present technique for treating vertebral fractures may include creating an access channel into a vertebral body. FIG. 1 illustrates a cannula assembly 10 that may be used to create an access channel through a patient's tissue to a vertebral body (not illustrated) in accordance with one embodiment of the present invention. In the illustrated embodiment, the cannula assembly 10 comprises a cannula 20 configured to allow passage of various instruments and materials into the vertebral body. The cannula 20 may have a proximal end 30 and a distal end 40. The cannula assembly 10 further may include a stylet 50 removably disposed in the cannula 20. As illustrated, the stylet 50 may have a pointed end 60 that extends beyond the distal end 40 of the cannula 20. In an embodiment, the cannula assembly 10 may further comprise a handle 70 disposed on the proximal end of the cannula 20. In an embodiment, the cannula assembly 10 may be a trocar-tipped cannula. By way of example, the cannula assembly 10 may be a diamond, scoop, bevel, trocar tipped cannula.

To create the access channel, the physician may make an incision in the patient's back, for example. The distal end 40 of the cannula 20 may be inserted into the incision. The physician may then apply longitudinal force to the cannula assembly 10 while rotating the handle 70 to advance the cannula 20 through the patient's tissue and into a vertebral body. In other embodiments, the handle 70 may use other mechanisms to advance the cannula 20 through the patient's tissue, such as a ratcheting system. In an embodiment, the cannula 20 may be inserted into the vertebral body through a pedicle. Once the cannula 20 has been inserted into the vertebral body, the stylet 50 and handle 70 may be removed, leaving the cannula 20. In this manner, the cannula 20 may provide an access channel into the vertebral body.

Figure 2:
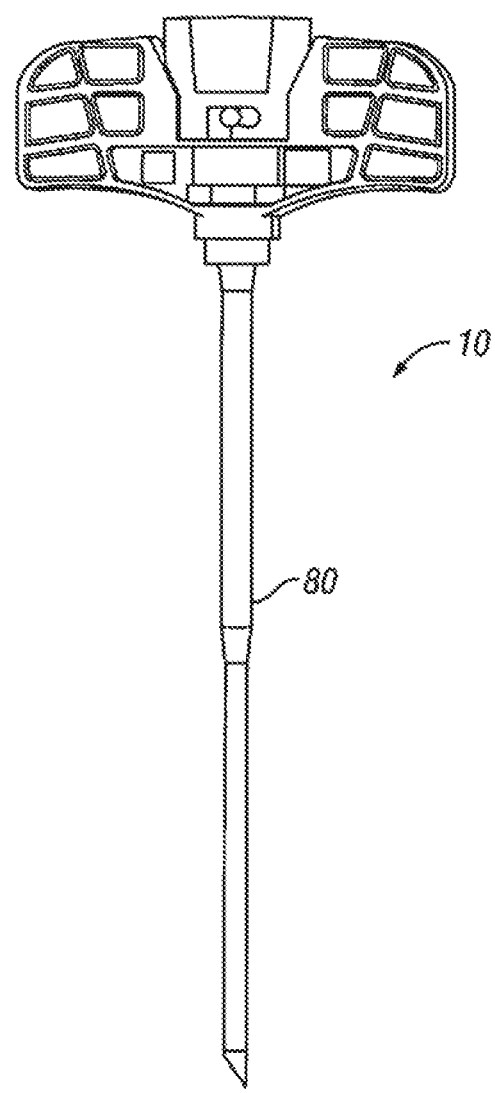
FIG. 2 illustrates a cannula assembly having a tapered cannula in accordance with one embodiment of the present invention.

While the cannula assembly 10 may be suited for creating an access channel to vertebral bodies in all regions of the vertebral column, the cannula assembly 10 may be particularly suited for access in the middle of the thoracic region and lower. If access is desired from the middle of the thoracic region and above, a device having a tapered cannula may be used, in accordance with one embodiment. FIG. 2 illustrates a cannula assembly 10 having a tapered cannula 80 in accordance with an embodiment of the present invention. While the tapered cannula 80 may be particularly suited for accessing the middle of the thoracic region and above, it should be understood that the tapered cannula 80 may also be used to create an access channel to vertebral bodies in all regions of the vertebral column.

While FIG. 1-2 describe use of a cannula assembly 10 that is sharp and pointed for creating an access channel into a vertebral body, it should be understood that a variety of different devices and techniques may be used to create the access channel in accordance with embodiment of the present invention. Referring now to FIGS. 3-6, an alternative technique for creating an access channel into a vertebral body is illustrated in accordance with one embodiment of the present invention.

Figures 3, 4:
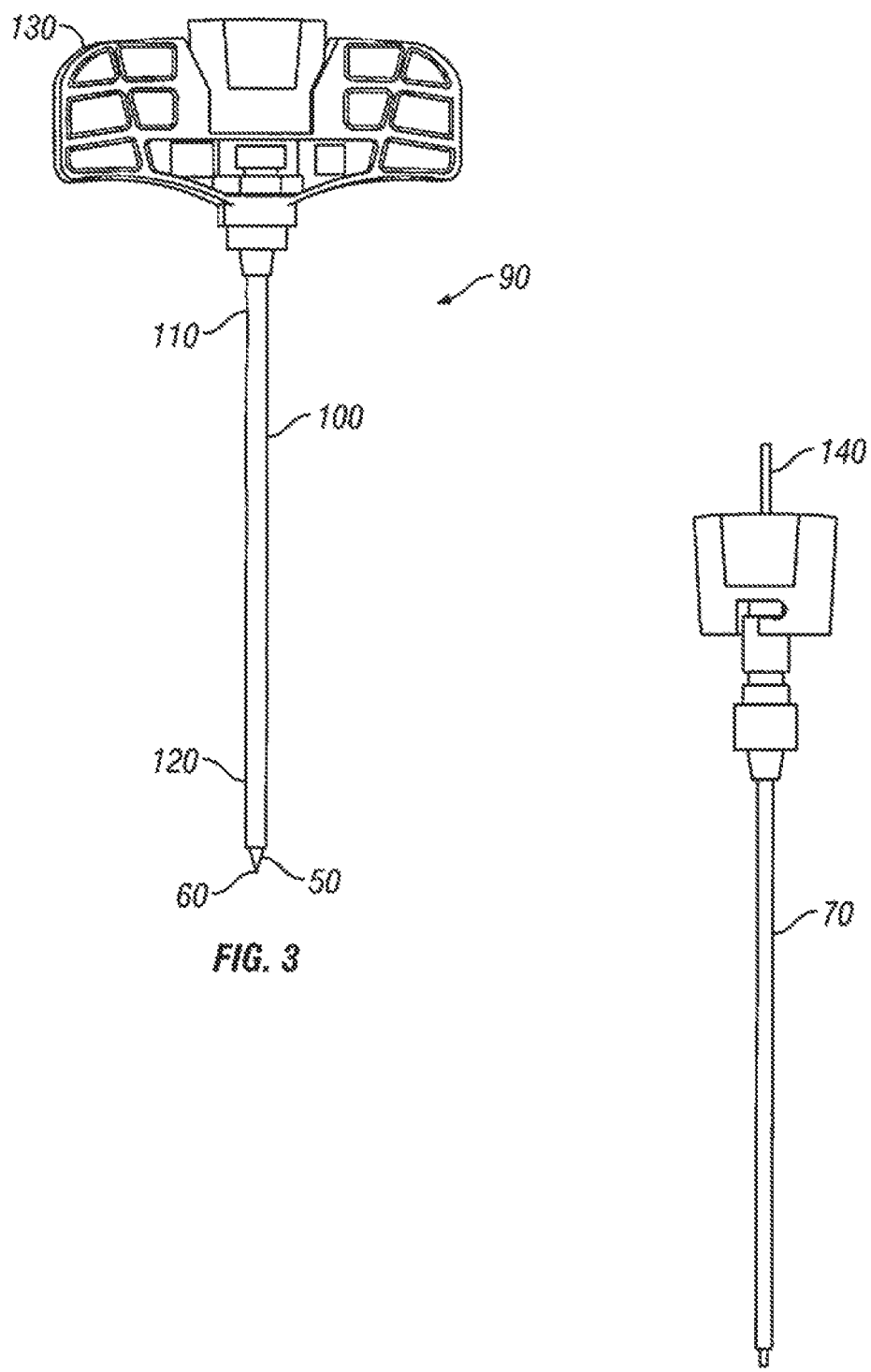
FIG. 3 illustrates a needle assembly in accordance with one embodiment of the present invention.
FIG. 4 illustrates a needle assembly having a guide wire disposed therethrough in accordance with one embodiment of the present invention.

FIG. 3 illustrates a needle assembly 90 that may be used to create an access channel through a patient's tissue to a vertebral body (not illustrated) in accordance with an embodiment of the present invention. In the illustrated embodiment, the needle assembly 90 comprises a needle 100 having a proximal end 110 and a distal end 120. The needle assembly 90 further may include a stylet 50 removably disposed in the needle 100. As illustrated, the stylet 50 may have a pointed end 60 that extends beyond the distal end 120 of the needle 100. As illustrated, the needle assembly 90 may further comprise a handle 130 disposed on the proximal end 110 of the needle 100. In an embodiment, the needle assembly 90 is a diamond, bevel tipped Jamshidi needle.

The needle assembly 90 of FIG. 3 may be inserted into the vertebral body in a similar manner to the cannula assembly 10 of FIG. 1. By way of example, the distal end 120 of the needle 100 may be inserted into an incision in the patient's back. To advance the needle 100 into the vertebral body, longitudinal force may then be applied to the needle assembly 90 while rotating the handle 130. The stylet 50 and handle 130 may then be removed, leaving the needle 100. As illustrated by FIG. 4, a guide wire 140 (e.g., a k-wire) may be disposed through the needle 100 and into the vertebral body. With the guide wire 140 in place, the needle 100 may be removed.

Figure 5:
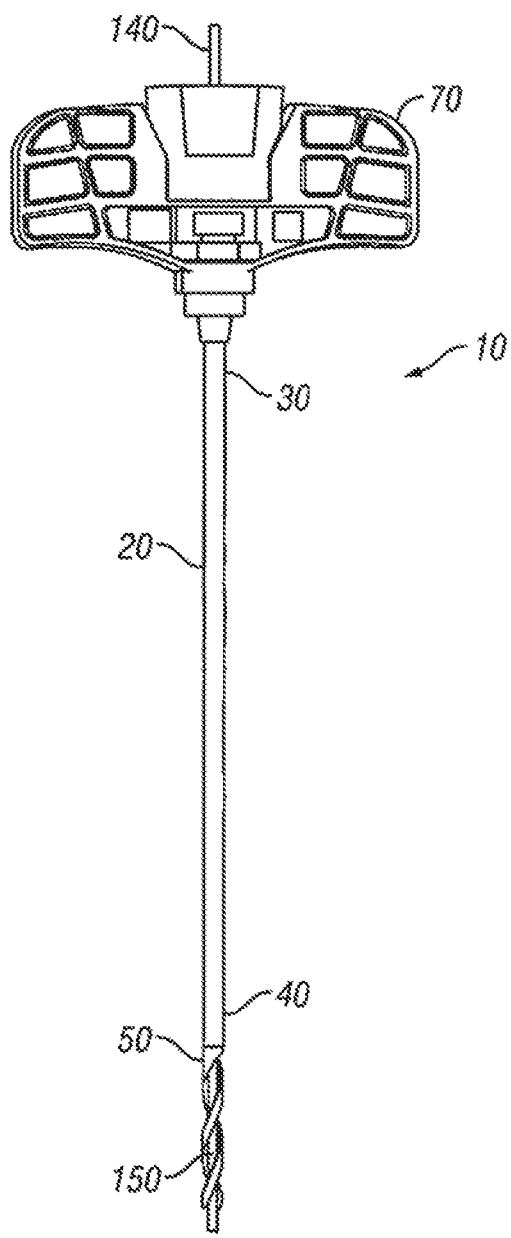
FIG. 5 illustrates a cannula assembly disposed over a guide wire and having a drill-tip stylet in accordance with one embodiment of the present invention.
Figure 6:
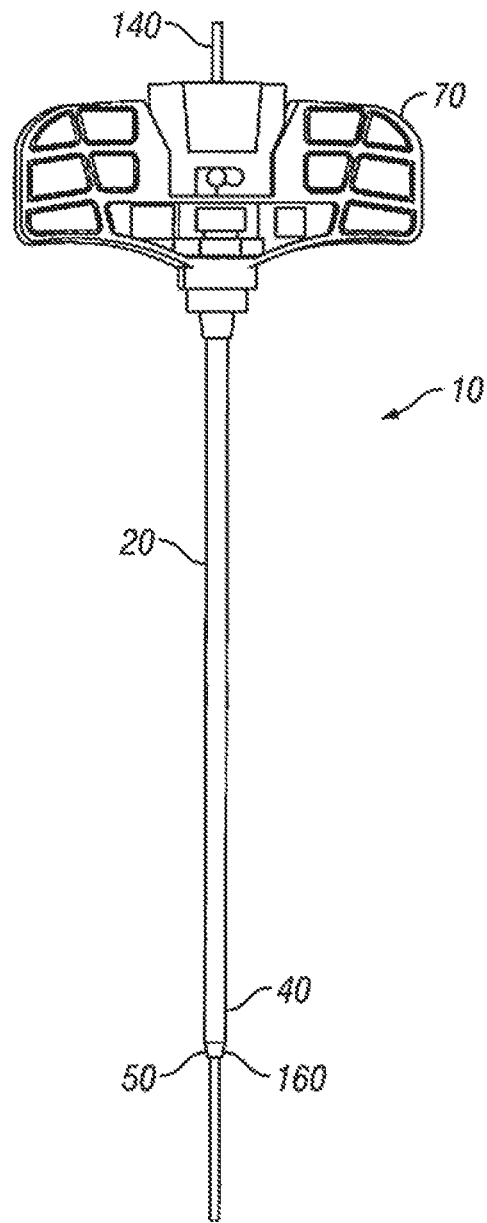
FIG. 6 illustrates a cannula assembly disposed over a guide wire and having a conical-tip stylet in accordance with one embodiment of the present invention.

As illustrated by FIG. 5, after removal of the needle 100, a cannula assembly 10 may be inserted over the guide wire 140 and into the vertebral body. In the illustrated embodiment, the cannula assembly 10 includes a cannula 20 having a handle 70 disposed on the proximal end 30. In an embodiment, a stylet 50 having a drill-shaped end 150 may be disposed in the cannula 20. As illustrated, the drill-shaped end 150 of the stylet 50 may extend out from the distal end 40 of the cannula 20. FIG. 6 illustrates an alternative embodiment of the cannula assembly 10. As illustrated by FIG. 6, the stylet 50 disposed in the cannula 20 may have a conically shaped end 160 extending out from the distal end 40 of the cannula 20. To advance the cannula assembly 10 over the guide wire 140 and through the patient's tissue, the physician may apply longitudinal force to the cannula assembly 10 while rotating the handle 70. Once the cannula assembly 10 has been inserted into the vertebral body, the stylet 50, handle 70, and guide wire 140 may be removed, leaving the cannula 20. In this manner, the cannula 20 may provide an access channel into the vertebral body.

Figure 7:
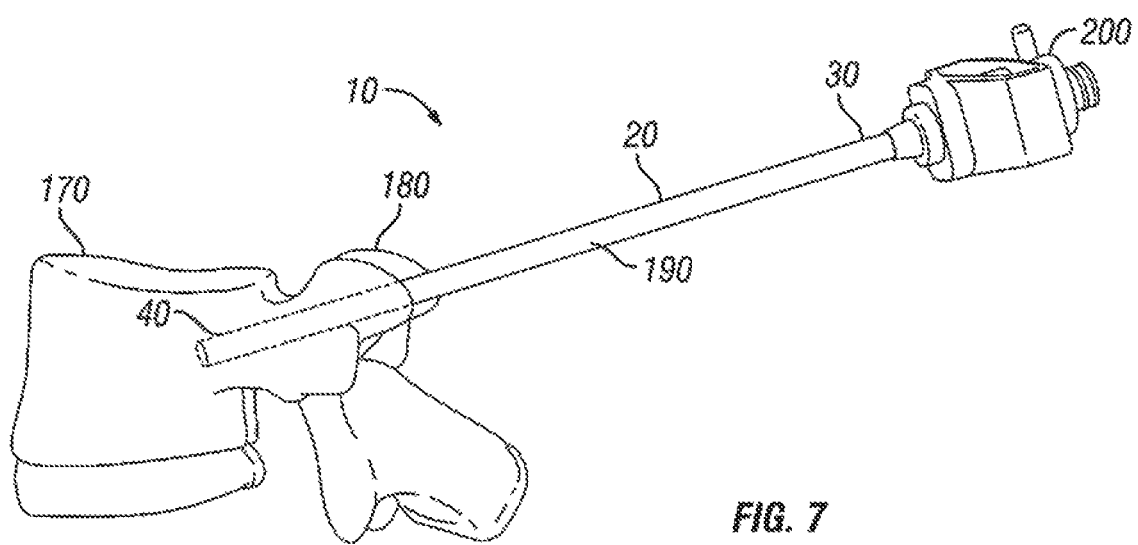
FIG. 7 illustrates a cannula assembly inserted into a vertebral body in accordance with one embodiment of the present invention.

FIG. 7 illustrates a cannula assembly 10 that has been inserted into a vertebral body 170 to provide access to the vertebral body 170 in accordance with one embodiment of the present invention. In an embodiment, the cannula assembly 10 may be inserted into the vertebral body 170 through a pedicle 180. In an embodiment (not illustrated), the cannula assembly 10 is not inserted through the pedicle 180. In the illustrated embodiment, the cannula assembly 10 includes a cannula 20 having a proximal end 30 and a distal end 40 extending into the vertebral body 170. As illustrated, cannula 20 may include an inner lumen 190 configured to allow passage of various instruments and materials into the vertebral body 170. The cannula assembly 10 further may include a cannula hub 200 disposed on the proximal end 30 of the cannula 20.

Figure 8:
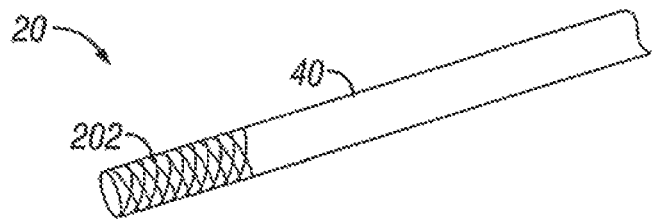
FIG. 8 illustrates a cannula assembly having knurling at the distal end in accordance with one embodiment of the present invention.
Figure 9:
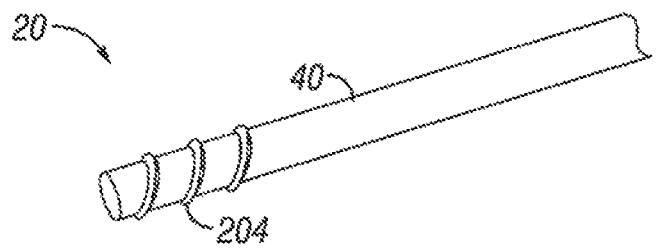
FIG. 9 illustrates a cannula assembly having threading at the distal end in accordance with one embodiment of the present invention.
Figure 10:
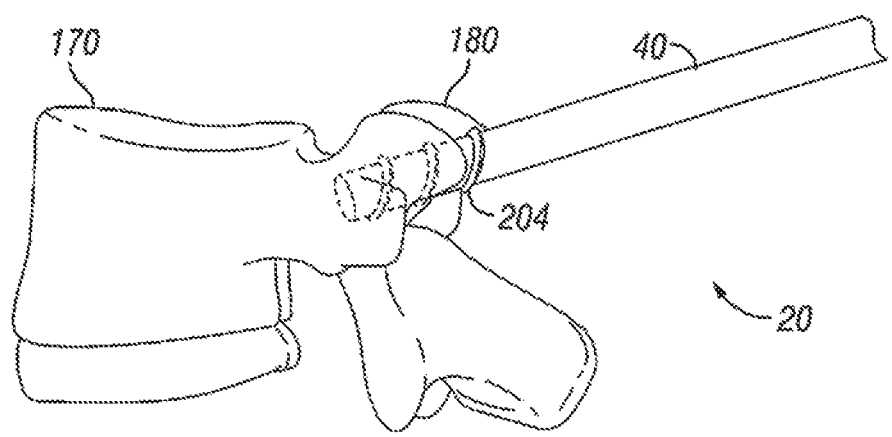
FIG. 10 illustrates a cannula assembly having the threading that has been inserted into a vertebral body in accordance with one embodiment of the present invention.

Embodiments of the present technique include a gripping feature at the distal end 40 of the cannula 20 that can, for example, thread into bone (e.g., pedicle 180) during insertion there through. In this manner, movement and/or slippage of the cannula 20 can be reduced or even prevented. FIG. 8 illustrates cannula 20 having knurling 202 at the distal end 40. FIG. 9 illustrates cannula 20 having threading 204 at the distal end 40. As illustrated by FIG. 10, the threading 204 can thread into the bone of the pedicle 180 during insertion into the vertebral body 170. In a similar manner, the knurling of FIG. 8 also threads into the bone during insertion. Alternative embodiments (not illustrated) may include a gripping feature created by grit blasting or laser ablating a portion of the distal end 40 of the cannula 20.

Figure 11:
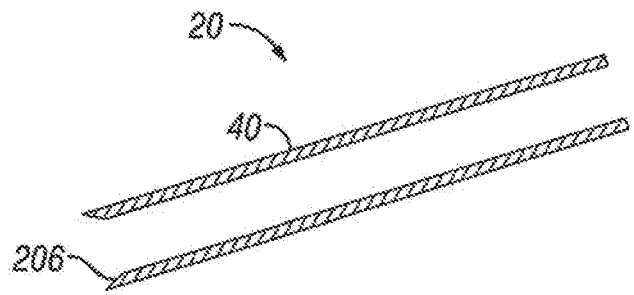
FIG. 11 illustrates a cannula assembly having a tapered end in accordance with one embodiment of the present invention.
Figure 12:
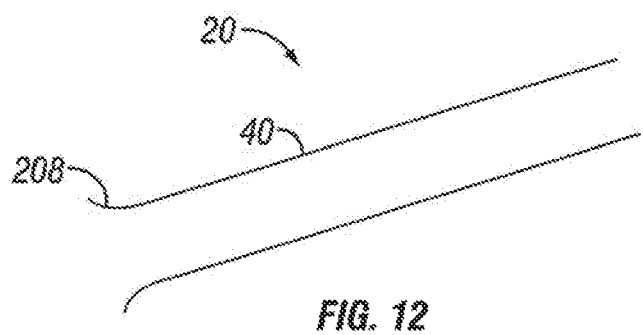
FIG. 12 illustrates a cannula assembly having a flared end in accordance with one embodiment of the present invention.
Figure 13:
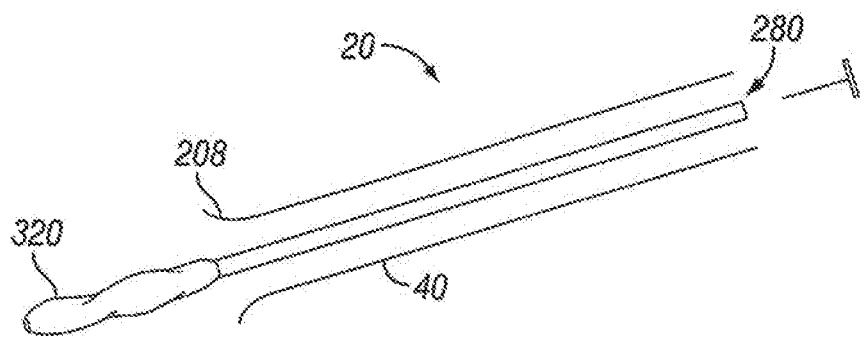
FIG. 13 illustrates removal of a balloon assembly from a cannula assembly having a flared end in accordance with one embodiment of the present invention.

Embodiments of the present technique may also include flaring or tapering at the distal end 40 of the cannula 20. The flaring/tapering may, for example, facilitate withdrawal of balloon(s) from the cannula 20. FIG. 11 illustrates cannula 20 having tapering 206 at the distal end 40. FIG. 12 illustrates cannula 20 having flaring 208 at the distal end 40. As illustrated by FIG. 13, withdrawal of balloon assembly 280 from the cannula 20 may be facilitated by the flaring 208. For example, folding of the balloon 320 during withdrawal may be improved with the flaring 208 at the distal end 40. In a similar manner, the tapering 206 of FIG. 11 can also improve folding of the balloon 320 during its removal. Balloon assembly 280 is described in more detail below with respect to FIG. 16.

Embodiments of the present technique for treating vertebral fractures may further include creating a channel in the vertebral body 170. FIG. 14 illustrates a drill 210 that may be used to create the channel in the vertebral body 170 in accordance with one embodiment of the present invention. In the illustrated embodiment, the drill 210 comprises a shaft 220 having a proximal end 230 and a distal end 240. A bit 250 may extend from the distal end 240 of the shaft 220. A handle 260 may be disposed on the proximal end 230 of the shaft. As illustrated by FIG. 15, the drill 210 may be used to create a channel 270 in the vertebral body 170. By way of example, the physician may insert the drill 210 through the inner lumen 190 of the cannula 20 until the bit 250 contacts bone (e.g., cancellous bone) within the vertebral body 170. The channel 270 in the vertebral body 170 may then be created by application of longitudinal forces to the drill 210 while rotating the handle 260. The drill 210 may then be removed from the cannula 20 leaving the cannula assembly 10 in place, for example, with the cannula 20 providing access to the channel 270 within the vertebral body 170.

Figure 16:
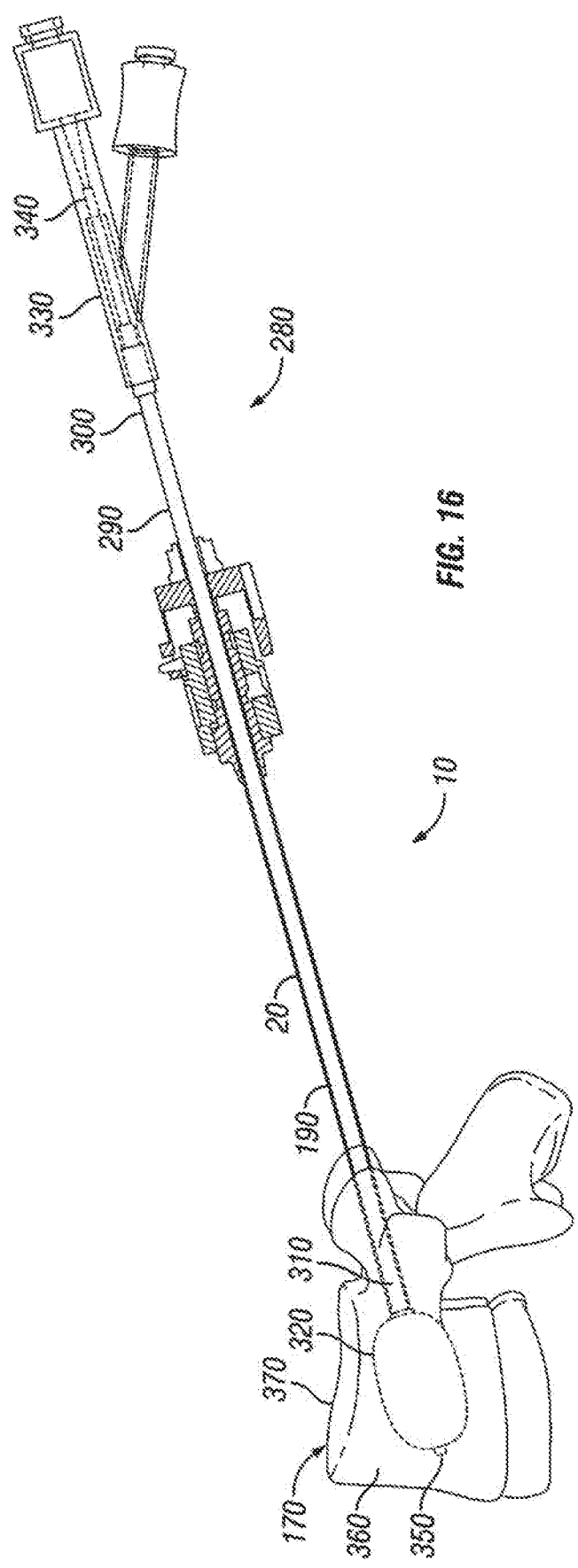
FIG. 16 illustrates insertion of a balloon into a vertebral body in accordance with one embodiment of the present invention.

Embodiments of the present technique for treating vertebral fractures may further include creating a cavity in a vertebral body 170. FIG. 16 illustrates creation of a cavity in vertebral body 170 with a balloon assembly 280 in accordance with one embodiment of the present invention. As illustrated, cannula assembly 10 has been inserted into the vertebral body 170 with the cannula 20 providing access into the vertebral body 170. To create the cavity, balloon assembly 280 may be inserted into the previously created channel 270 (illustrated on FIG. 15 in the vertebral body 170 through the inner lumen 190 of the cannula 20. In certain embodiments, the balloon assembly 280 may be an inflatable bone tamp. In the illustrated embodiment, the balloon assembly 280 includes a catheter 290 having a proximal end 300 and a distal end 310. A balloon 320 may be attached to the distal end 310 of the catheter 290. While FIG. 16 illustrates the balloon 320 in an expanded configuration, it should be understood that the balloon 320 should be inserted into the vertebral body 170 in a deflated state. The balloon 320 used to create the cavity may include any of a variety of different balloons suitable for use in medical procedures. Examples of suitable balloons include those commonly used in kyphoplasty, including those comprising plastics, composite materials, polyethylene, rubber, polyurethane, or any other suitable material. As illustrated, the balloon assembly 280 may further include an inner lumen 340 disposed within the catheter 290. As illustrated, the inner catheter 330 has an inner lumen 340 with an exit port 350, for example, that extends beyond the balloon 320.

As illustrated by FIG. 16, the balloon 320 may be inflated, for example, to compact the cancellous bone 360 in the interior portion of the vertebral body 170 enlarging the channel (illustrated on FIG. 15) to create a cavity within the vertebral body 170. In addition to creation of the cavity, the balloon 320 may also, for example, force apart the compact bone 370, restoring height to the vertebral body 170. After cavity creation, the balloon 320 may be deflated and removed from the vertebral body 170.

Figure 17:
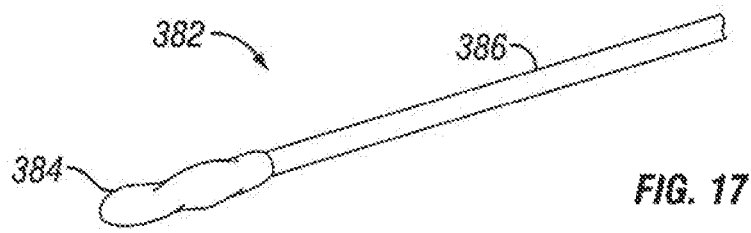
FIG. 17 illustrates an assembly having a jacket at a distal end in accordance with one embodiment of the present invention.
Figure 18:
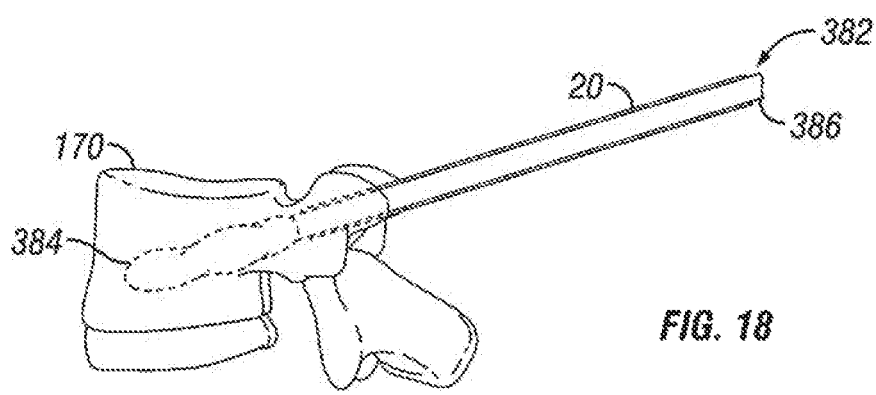
FIGS. 18-20 illustrate creation of a cavity in a vertebral body in accordance with one embodiment of the present invention.
Figure 19:
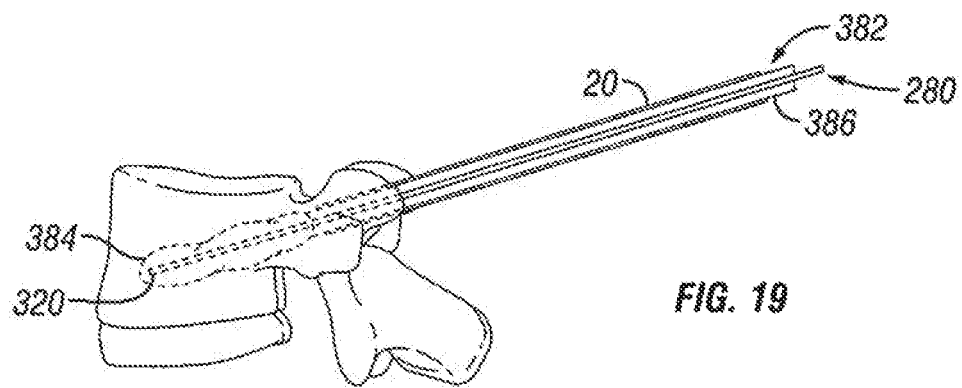
Figure 20:
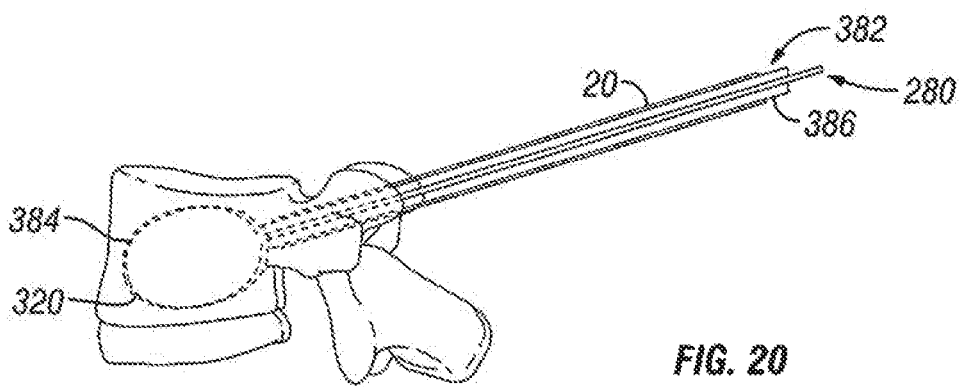

FIGS. 17-20 illustrate an alternative embodiment for employing balloon assembly 280 to create a cavity with the vertebral body 170. The method illustrated by FIGS. 17-20 utilizes a jacket assembly 382 into which the balloon assembly 280 may be inserted to make the cavity. This technique may be desirable, for example, in very hard bone in which the balloon assembly 280 may not be inflated to sufficient pressure for cavity creation. As illustrated by FIG. 17, the jacket assembly 382 may comprise a jacket 384 disposed on an end of a tube 386. In an embodiment, the jacket 384 may be stitched onto the end of the tube 386. The jacket 384 may comprise a variety of different materials, including, for example, polyethylene terephthalate and ultra-high molecular weight polyethylene. In an embodiment, the jacket 384 is a microporous textile. FIG. 18 illustrates insertion of the jacket assembly 382 into the vertebral body 170 through the cannula 20. With the jacket assembly 382 in place, the balloon 320 may be placed into the jacket 384. As illustrated by FIG. 19, the balloon 320 may be disposed on the end of the balloon assembly 280. The balloon 320 may then be inflated (see, e.g., FIG. 20) to create a cavity within the vertebral body 170. In addition to creation of the cavity, the balloon 320 may also, for example, restore height to the vertebral body 170. After cavity creation, the balloon 320 may be deflated and removed from the vertebral body 170.

Figure 21:
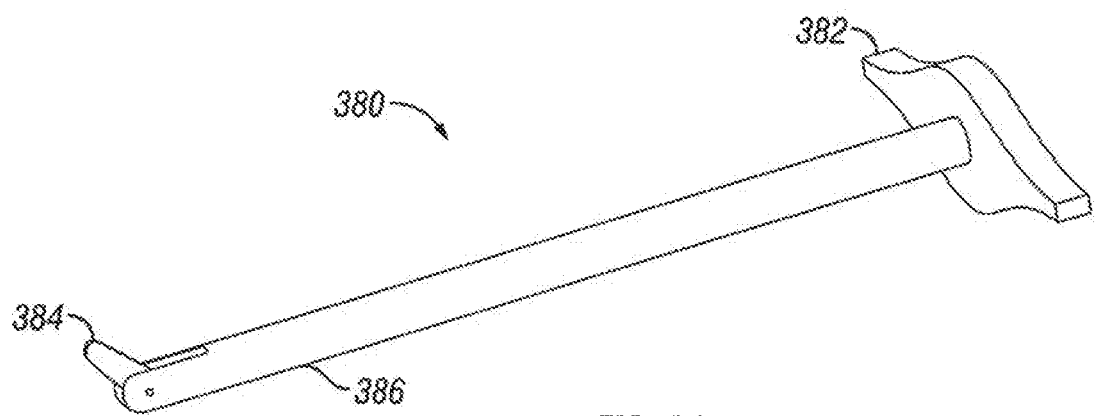
FIG. 21 illustrates a mechanical device having a single-arm cutting mechanism that can be used to create a cavity in a vertebral body in accordance with one embodiment of the present invention.
Figure 22:
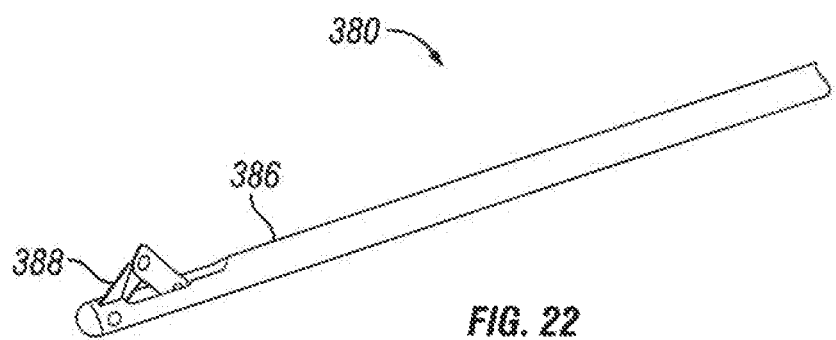
FIG. 22 illustrates a mechanical device having a double-arm cutting mechanism that can be used to create a cavity in a vertebral body in accordance with one embodiment of the present invention.
Figure 23:
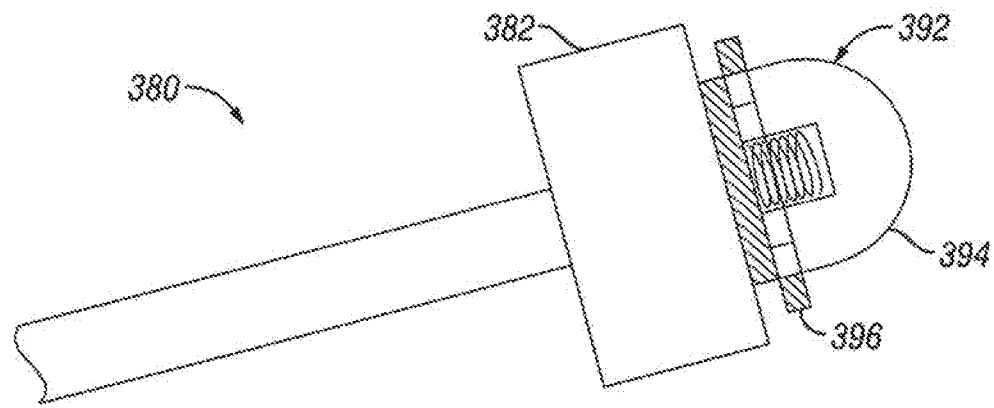
FIG. 23 illustrates a handle assembly that can be used with embodiments of the mechanical devices of FIGS. 21 and 22 in accordance with one embodiment of the present invention.
Figure 24:
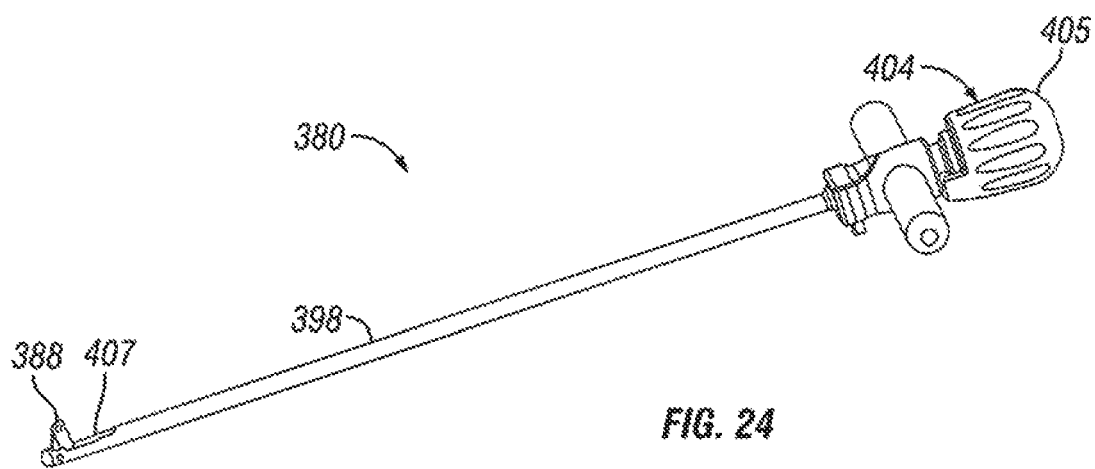
FIGS. 24-29 illustrate a mechanical device having a double-arm cutting mechanism that can be used to create a cavity in a vertebral body in accordance with embodiments of the present invention.
Figure 25:
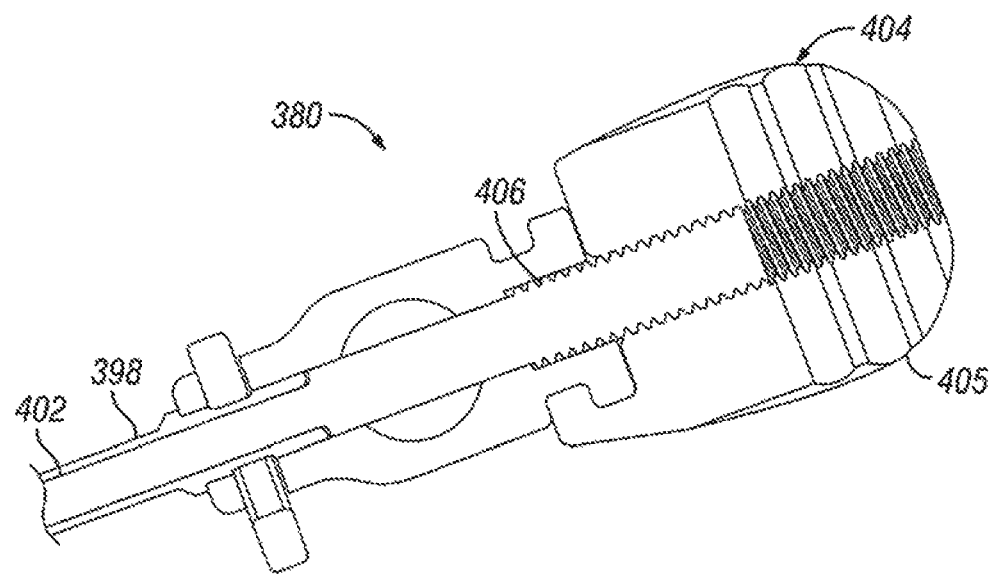

While FIGS. 16-20 illustrates the use of the balloon assembly 280 for creation of the cavity in the vertebral body 170, those of ordinary skill in the art will appreciate that other suitable techniques may also be used for creation of the cavity. By way of example, an expandable jack or other suitable mechanical device may be used to create the cavity in the vertebral body 170. FIG. 21 illustrates an embodiment of a mechanical device 380 that may be used to create the cavity in accordance with one embodiment of the present invention. In the illustrated embodiment, the mechanical device 380 includes a handle assembly 382 on one end and a single-arm cutting mechanism 384 at its distal end 386. Alternatively, as illustrated by FIG. 22, the mechanical device 380 may include a double-arm cutting mechanism 388 at its distal end 386. In an embodiment, the mechanical device 380 may be inserted through the cannula assembly 10 and into the vertebral body 170. The mechanical device 380 may then be activated to create the cavity. FIG. 23 illustrates an embodiment of the handle assembly 382 of the mechanical device 380 in more detail. As illustrated, the handle assembly 382 includes an actuator 392 having a depressible head 394. To activate the cutting mechanism (e.g., single-arm cutting mechanism 384, double-arm cutting mechanism 388), the depressible head 394 may be actuated by pushing down. With the head 394 in the depressed position, a locking pin 396 may be inserted to lock the cutting mechanism in the activated (or cutting) position. Another embodiment of a mechanical device that can be used for cavity creation is a cutting device 640 illustrated by FIG. 71. As discussed in more detail below, the cutting device 640 includes a cutting wire 700 than can be extended from main body 720.

Figure 26:
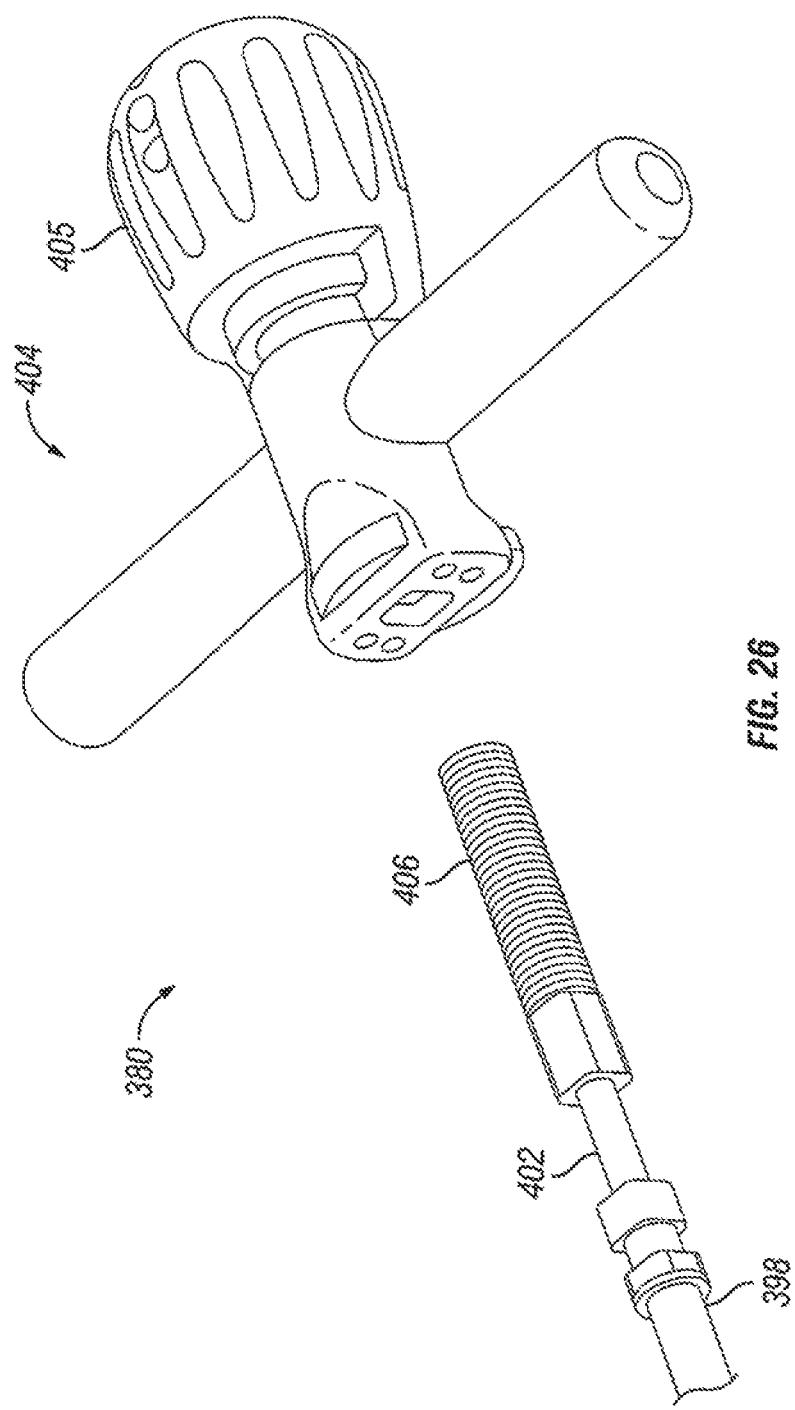
Figure 27:
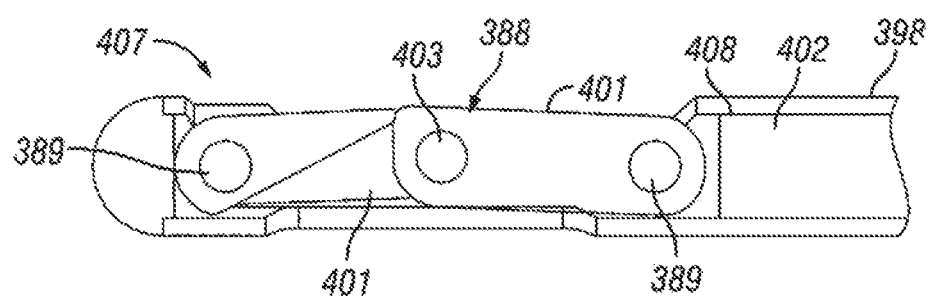
Figure 28:
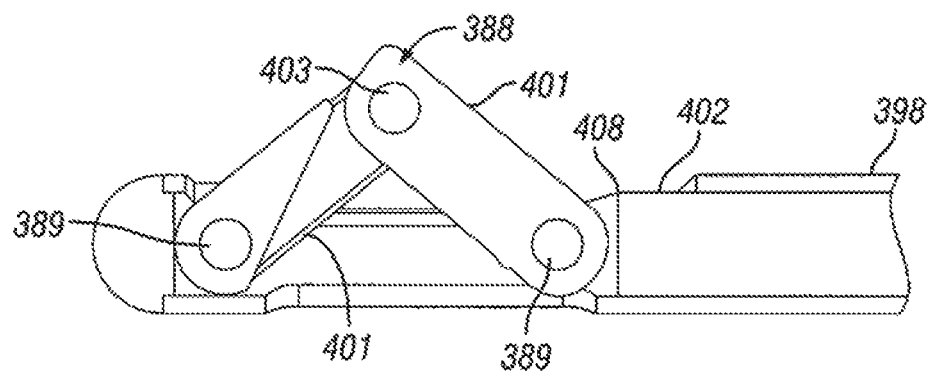
Figure 29:
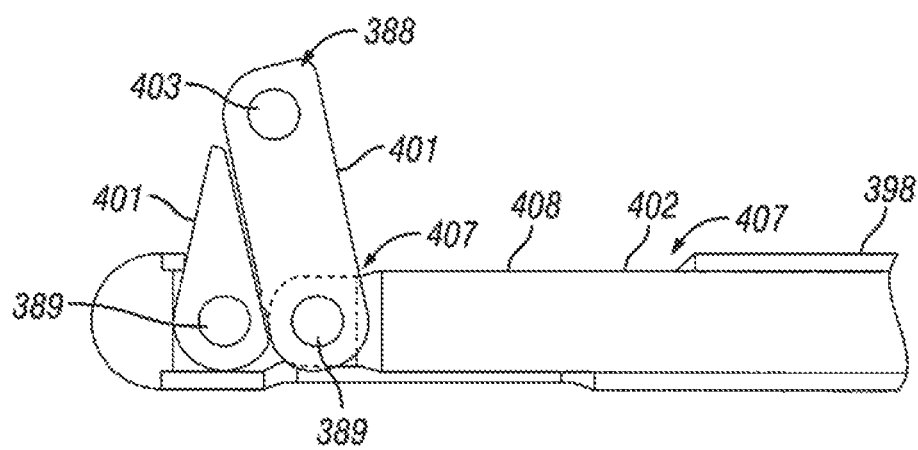

FIGS. 24-28 illustrate an embodiment of a mechanical device 380 having a double-arm cutting mechanism 388. As illustrated, the mechanical device 380 may include outer tube 398, connecting rod 402, handle assembly 404, and double-arm cutting mechanism 388. Connecting rod 402 having proximal end 406 and distal end 408 may be disposed inside outer tube 398. Handle assembly 404 may be disposed at the proximal end 406 of the connecting rod 402. In an embodiment, the handle assembly 404 is coupled to the outer tube 398. The handle assembly 404 may be coupled to the outer tube 398, for example, by a spring-loaded slide lock (not illustrated). As illustrated, the handle assembly 404 may include handle ball 405. The handle ball 405 may be threaded onto the distal end 408 of the connecting rod 402. Double-arm cutting mechanism 388 may be disposed at the distal end 408 of the connecting rod 402. Double-arm cutting mechanism 388 may include blades 401 coupled by hinge 403. The double-arm connecting mechanism 388 may include hinges 389 coupled to the connecting rod 402. In the illustrated embodiment, the double-arm cutting mechanism 388 includes two blades 401 that are each coupled to the connecting rod 402 by a corresponding one of the hinges 389. The blades 401 may be configured, for example, to extend through slot 407 in outer tube 398 when the hinges 389 are pushed together, as illustrated by FIGS. 27-28.

Embodiments of the present invention may include inserting the mechanical device 380 illustrated by FIGS. 24-28 into a vertebral body. When inserted through a cannula and into a vertebral body, the double-arm cutting mechanism 388 may be in an unexpanded state, as illustrated by FIG. 26. After insertion, the hinges 403 of the double-arm cutting mechanism 388 may be forced together to extend the blades 401 through the slot 407 in the outer tube 398, as illustrated by FIGS. 27-28. The connecting rod 402 may be pushed through the outer tube 398 to push the hinges 403 together. As the handle ball 405 is turned, the connecting rod 402 should be pushed through the outer tube 398 collapsing the hinges 403. As illustrated, the blades 401 may extend through the slot 407 in an arch. The blades 401 can then be rotated to cut a cavity in the vertebral body. In an embodiment, the blades 401 may cut the bone in a cylindrical shape.

Figure 30:
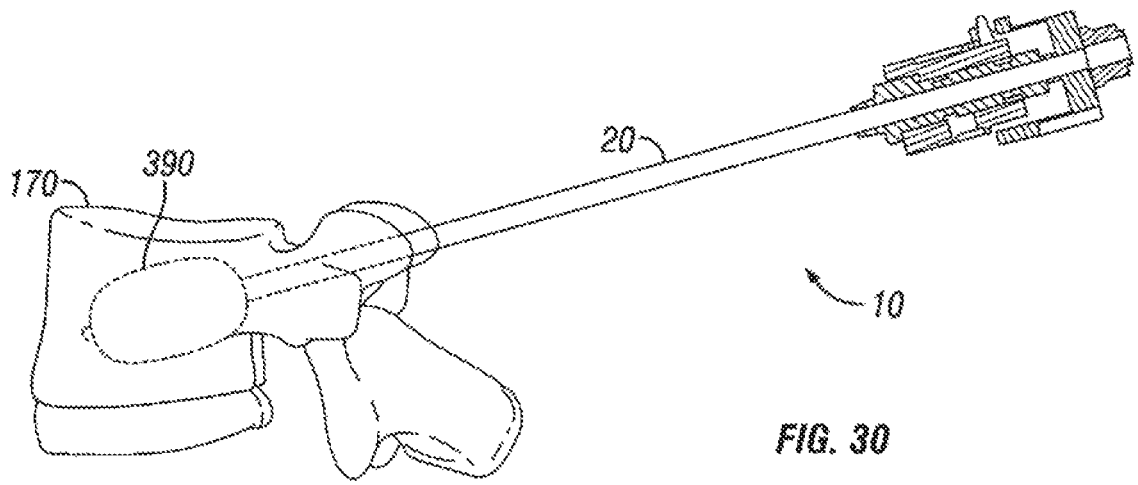
FIG. 30 illustrates a cavity in a vertebral body in accordance with one embodiment of the present invention.

FIG. 30 illustrates a cavity 390 that has been created in the vertebral body 170 in accordance with one embodiment of the present invention. In accordance with present embodiments, the cavity 390 may be formed using an inflatable balloon, a mechanical device, or a combination of both. As illustrated, the cannula 20 of the cannula assembly 10 should extend into the cavity 390, providing access to the cavity 390. While not illustrated, embodiments of the present invention further may include coating the wall of the cavity 390 with a bone growing agent.

In accordance with embodiments of the present invention, a filler material may be introduced into the cavity 390, for example, to stabilize a fracture in the vertebral body 170. However, prior to insertion of the filler material, embodiments of the present technique further may include inserting a containment jacket into the cavity 390 in the vertebral body 170. The containment jacket may be employed to contain the filler material (e.g., cement) introduced into the cavity 390, for example, to prevent undesirable leakage. In this manner, problems associated with leakage of the filler material from the cavity 390.

Figure 31:
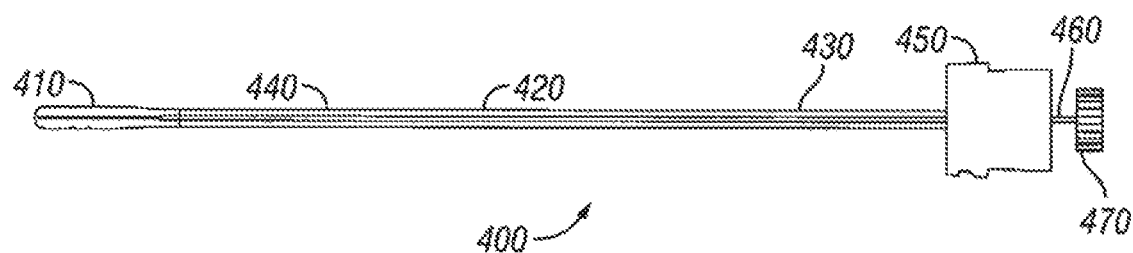
FIG. 31 illustrates a containment assembly in a wrapped/deflated state in accordance with one embodiment of the present invention.

FIG. 31 illustrates a containment assembly 400 having a containment jacket 410 that may be inserted into the cavity. As illustrated, the containment assembly 400 comprises a tubular member 420 (e.g., a cannula) having a proximal end 430 and a distal end 440. The tubular member 420 may be configured to allow passage of various instruments and materials into a vertebral body. The containment jacket 410 may be disposed on the distal end 440 of the tubular member 420. In the illustrated embodiment, the containment jacket 410 is in a deflated state. In an embodiment, the containment jacket 410 is impermeable, e.g., to the filler material. The containment jacket 410 may be constructed from any of a variety of suitable materials, including, for example, polyethylene, polyethylene terephthalate, thermoplastic elastomers (e.g., PEBAX® resins, BIONATE® PCU), silicon, polycaprolactone, polylactic acid, and nylon. It should be understood that the containment jacket 410 may be constructed from a material that bioresorbable or non-resorbable material in certain embodiments. As illustrated, a hub 450 may be disposed on the proximal end 430 of the tubular member 420. The hub 450 may allow connection of the containment assembly 400 to other devices that may be used in a medical procedure. A guide wire 460 (e.g., a K-wire) may be disposed through the tubular member 430. As illustrated, the guide wire 460 may extend into the proximal end 430 of the tubular member 420 and out from the distal end 440 of the tubular member 420. In an embodiment, the containment jacket 410 is disposed on the portion of the guide wire 460 extending from the distal end 440 of the tubular member 420. For example, the containment jacket 410 may be wrapped around the portion of the guide wire 460 extending through the distal end 440 of the tubular member 420. In this manner, the guide wire 460 may facilitate insertion of the containment jacket 410 through the cannula 20. In the illustrated embodiment, a cap 470 is disposed on the end of the guide wire 460 extending from the proximal end 430 of the tubular member 420.

Figure 32:
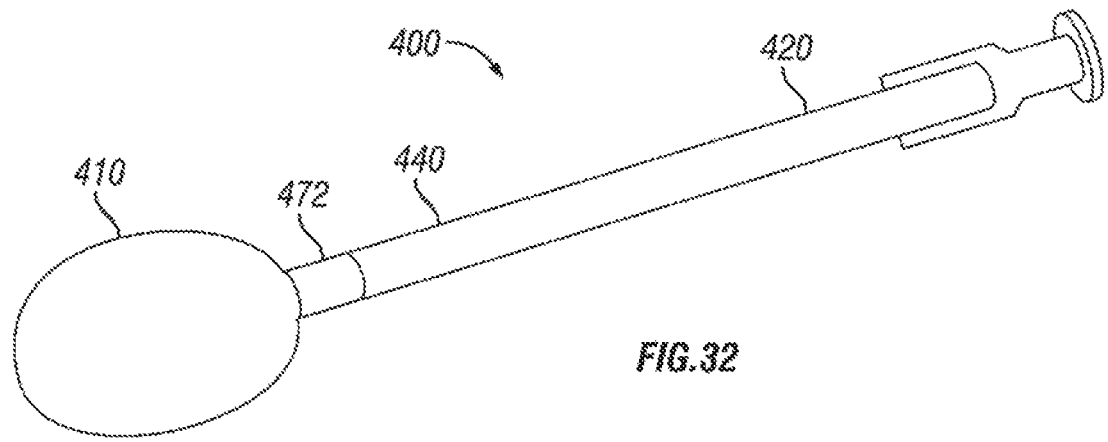
FIGS. 32-38 illustrate embodiments for attachment of a containment jacket to a tubular assembly.
Figure 33:
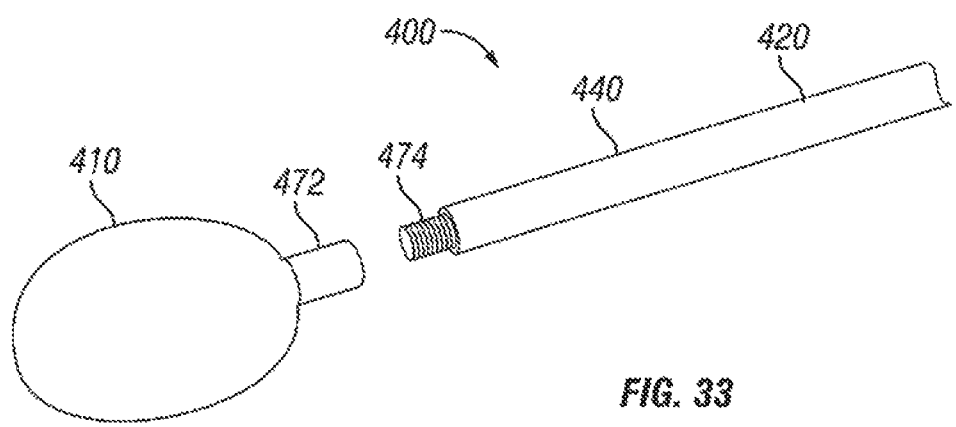

A variety of different techniques may be used in accordance with embodiments of the present technique for attachment of the containment jacket 410 to the tubular member 420. FIGS. 32-33 illustrate an embodiment of the containment assembly 400 that includes containment jacket 410 coupled to a distal end 440 of tubular member 420. As illustrated, the containment jacket 410 may include a neck 472 placed over the tip 474 of the distal end 440 of the tubular member 420. In an embodiment, an adhesive may be used to couple the neck 472 to the distal end 440. In an alternative embodiment, the neck 472 of the containment jacket 410 may be thermally bonded to the distal end 440 of the tubular member 420. As illustrated by FIG. 33, the tip 474 may be ground to, for example, facilitate flush bonding of the containment jacket 410 with the tubular member 420.

Figure 34:
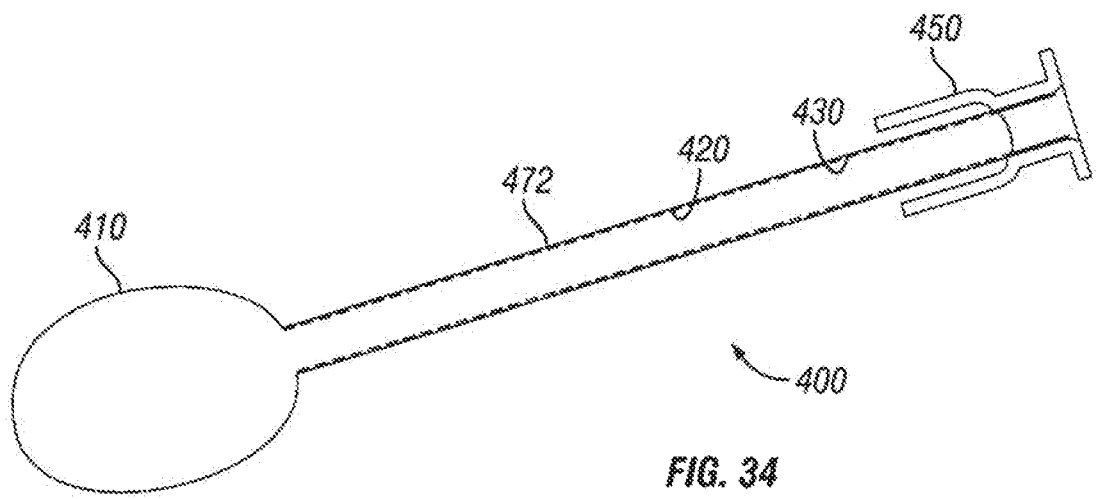
Figure 35:
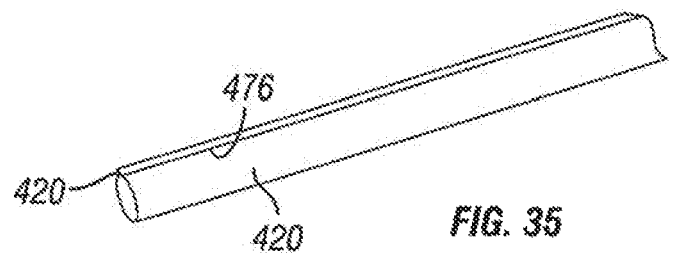
Figure 36:
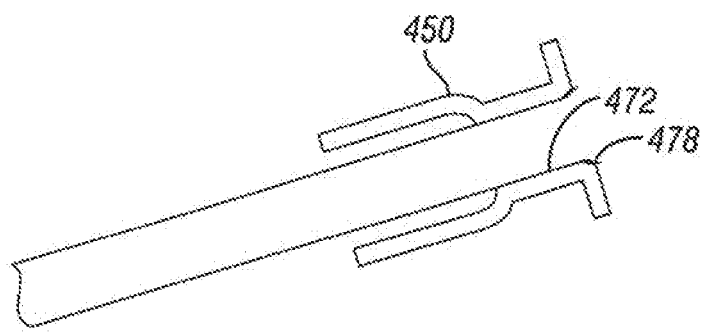

FIGS. 34-36 illustrate another technique for attachment of the containment jacket 410 to the tubular member 420 in accordance with one embodiment of the present invention. As illustrated by FIG. 34, the containment assembly 400 may include containment jacket 410 attached to the tubular member 420. A hub 450 may be disposed on the proximal end 430 of the tubular member 420. In the illustrated embodiment, the containment jacket 410 includes an elongated neck 472. In an embodiment, the elongated neck 472 may be welded to the tubular member 420. Any of a variety of different welding techniques may be suitable, including, for example, radio frequency welding, thermoforming, and ultrasonic welding. As illustrated by FIG. 35, a thin weld line 476 may couple the containment jacket 410 to the tubular member 420. In an embodiment, the containment jacket 410 may be coupled to the hub 450. As illustrated by FIG. 36, the distal end 478 of the elongated neck 472 may be coupled to the hub 450, for example, with an adhesive.

Figure 37:
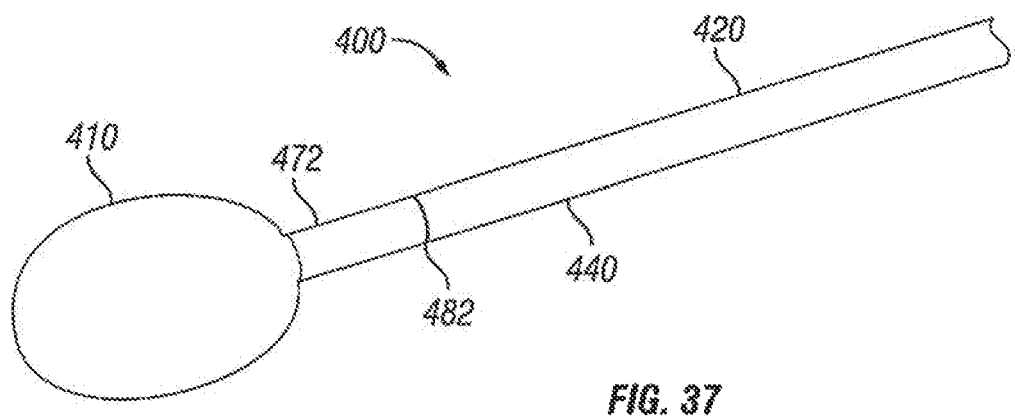

FIG. 37 illustrates yet another technique for attachment of the containment jacket 410 to the tubular member 420 in accordance with one embodiment of the present invention. In the illustrated embodiment, containment assembly 400 includes containment jacket 410 coupled to a distal end 440 of tubular member 420. As illustrated, a butt weld 482 may couple neck 472 of the containment jacket 410 to the distal end 440 of the tubular member 420.

Figure 38:
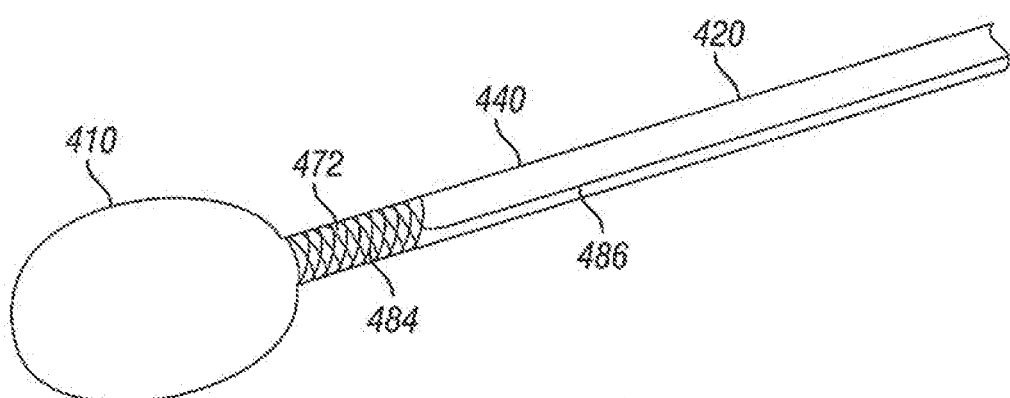

FIG. 38 illustrates yet another technique for attachment of the containment jacket 410 to the tubular member 420 in accordance with one embodiment of the present invention. As illustrated, thread 484 (e.g., suture thread) may be tied over the neck 472 of the containment jacket 410 to secure the containment jacket 410 onto the distal end 440 of the tubular member 420. A cord 486 may extend from the thread 484 that can be pulled to unravel the thread 484 releasing the containment jacket 410 from the tubular member 420.

Figure 39:
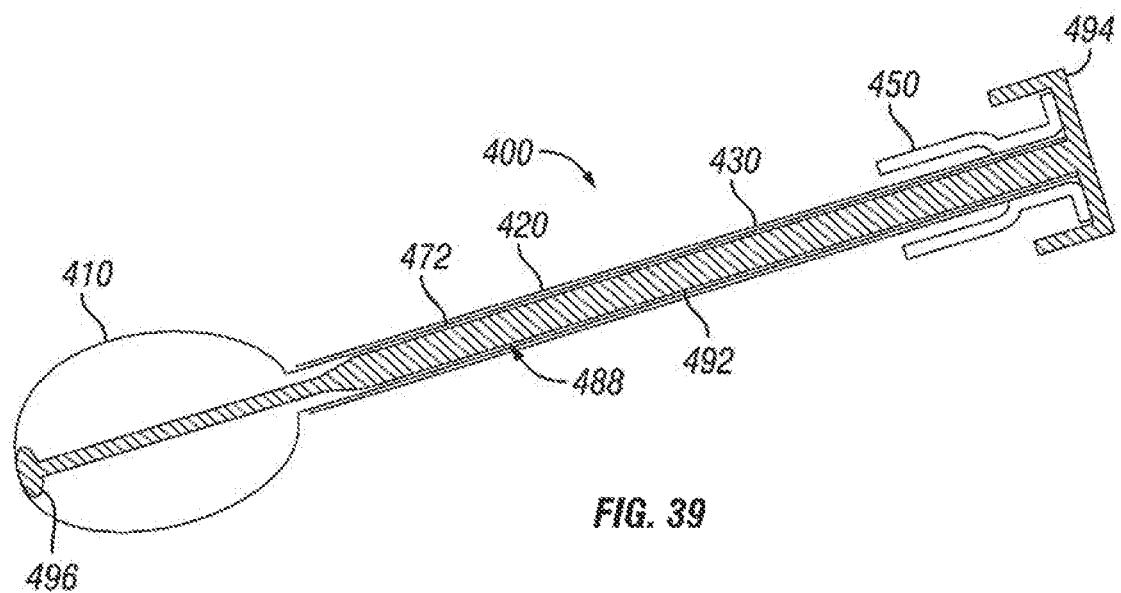
FIGS. 39-40 illustrate attachment of a containment jacket to a mandrel in accordance with one embodiment of the present invention.
Figure 40:
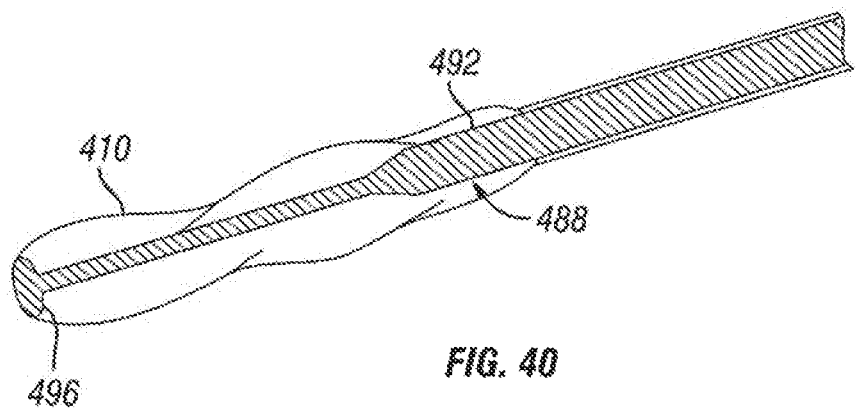

FIGS. 39-40 illustrate an alternate embodiment of the containment assembly 400 that can be used in accordance with one embodiment of the present invention. In the illustrated embodiment, the containment assembly 400 includes a tubular member 420 having a hub 450 on the proximal end 430. As illustrated, a mandrel assembly 488 may be disposed within the tubular member 420. In an embodiment, the mandrel assembly 488 may be constructed from a material that comprises polytetrafluoroethylene. The mandrel assembly 488 may comprise a stem 492 that extends through the tubular member 420. The mandrel assembly 488 may further comprise a mandrel hub 494 engaging the hub 450 of the tubular member 420. The mandrel assembly 488 may further comprise blunt nose 496 opposite the mandrel hub 494. The blunt nose 496 should reduce and/or prevent puncture of the containment jacket 410. The containment jacket 410 may enclose the blunt nose 496 with the neck 472 extending along the stem 492. As illustrated by FIG. 40, the containment jacket 410 may be wrapped around the stem 492 of the mandrel assembly 488. The mandrel assembly may, for example, facilitate insertion of the containment jacket 410 through the cannula 20 (e.g., shown on FIG. 30). After the containment jacket 410 has been inserted into the vertebral body 170, the containment jacket 410 may be unwrapped, as illustrated by FIG. 39.

Figure 41:
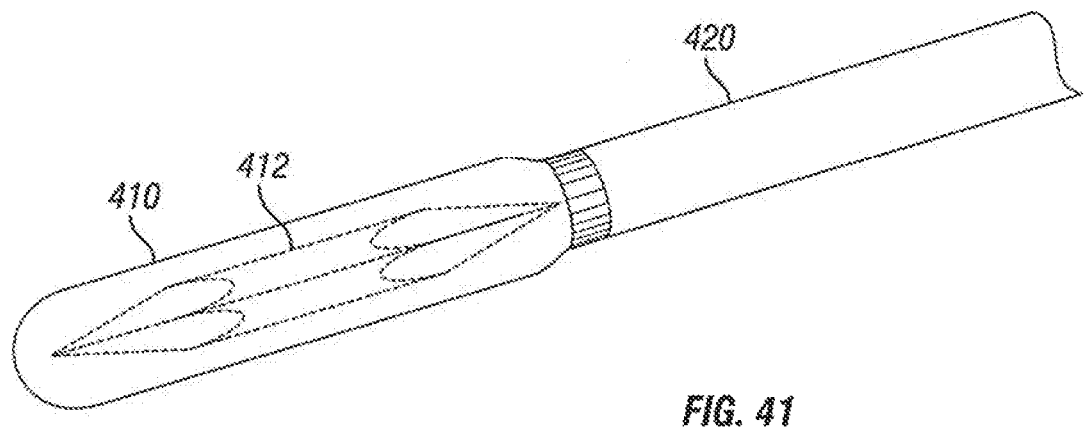
FIGS. 41-42 illustrate a containment jacket in accordance with one embodiment of the present invention.
Figure 42:
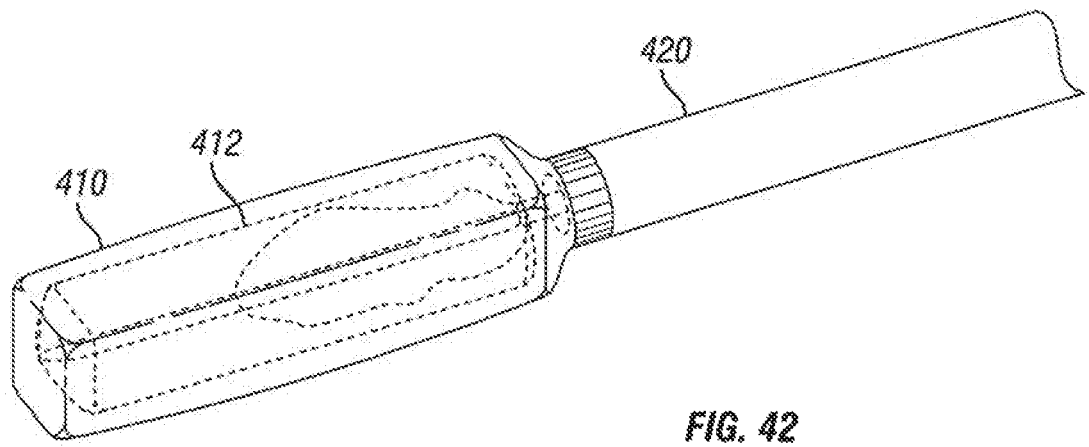
Figure 43:
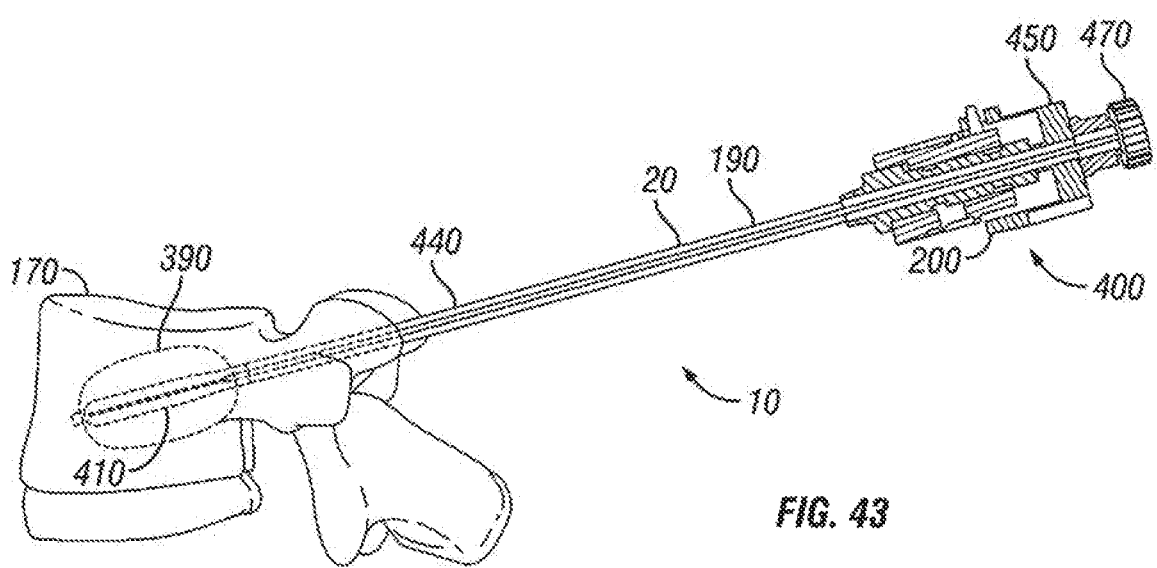
FIG. 43 illustrates insertion of a containment assembly into a vertebral body in accordance with one embodiment of the present invention.

FIGS. 41-42 an embodiment of a containment jacket 410 that may be used in accordance with embodiments of the present invention. As illustrated, the containment jacket 410 may be attached to tubular member 420. In an embodiment, the containment jacket 410 may be configured to a have pre-determined geometrical configuration when in an expanded state. For example, the containment jacket 410 may have a rectangular cross-section in an expanded state, as shown by FIG. 42. In other embodiments, the containment jacket 410 may be generally cylindrical in shape. In certain embodiments, the containment jacket 410 may be inserted into a disc space. Accordingly, embodiments of the containment jacket 410 may have lordosis and/or convexity to match the end plates of a disc space. In alternative embodiments, the containment jacket 410 may be inserted into a vertebral body 170, as illustrated by FIG. 43. It should be understood that the containment jacket 410 may also be inserted into other cavities within a bone as desired for a particular application.

In the embodiment illustrated by FIGS. 41-42, frame 412 may be used, for example, to reinforce the containment jacket 410 and provide the desired geometric configuration. As illustrated, the frame 412 may be disposed within the containment jacket 410. FIG. 41 illustrates the frame 412 in a collapsed state. In an embodiment, the frame 412 may have the property of shape memory such that, when the frame 412 is deployed, the containment jacket 410 expands to a pre-determined geometrical configured, as illustrated by FIG. 42. The internal frame 412 may be constructed from a material having the property of shape memory. Examples of suitable material include shape memory alloys, such as alloys of nickel and titanium.

As illustrated by FIG. 43, the containment jacket 410 may be inserted through the inner lumen 190 of the cannula 20 and into the cavity 390 within the vertebral body 170. In an embodiment, the containment jacket 410 may be in a wrapped/deflated state when it is inserted into the cavity 390. After insertion, the containment jacket 410 may be unwrapped/inflated, as illustrated by FIG. 43. In an embodiment, the frame 412 illustrated on FIGS. 41-42 may be deployed to expand the containment jacket 410 to a predetermined geometric configuration. The containment jacket 410 may be inserted by sliding the tubular member 440 with the containment jacket 410 disposed thereon through the cannula 20 of the cannula assembly 10. In an embodiment, the hub 450 on the containment assembly 400 may be coupled to the cannula hub 200 on the cannula assembly 10. As illustrated by FIG. 44, the hub 450 of the containment assembly 400 may threadedly engage the cannula hub 200. For example, the hub 450 may include female threads 502 that engage corresponding male threads 504 on the cannula hub 200. Once the containment jacket 410 has been placed, the guide wire 460 (e.g., shown on FIG. 31) or stem 492 (e.g., shown on FIG. 39), for example, may be removed from the containment assembly 400, leaving the containment jacket 410 in place. The cap 470 may be used to facilitate removal of the guide wire 460.

Embodiments of the present technique for treating vertebral fractures may further include removing fluid (e.g., air) from within the containment jacket 410 that has been placed into the vertebral body 170. Any of a variety of different techniques may be used to remove air from within the containment jacket. In an embodiment, a syringe may be used remove the air. An example of a suitable syringe includes a VacLok™ syringe. As illustrated by FIG. 45, a syringe 480 may be coupled to the hub 450 of the containment assembly 400. The plunger 490 of the syringe 480 may then be withdrawn to create a partial vacuum so that air from within the containment jacket 410 flows into the syringe 480. Accordingly, the fluid in the containment jacket 410 may be removed. To maintain the vacuum on the containment jacket 410, for example, a valve (e.g., a one-way valve) may be included in the hub 450. In an embodiment, the valve may hold at least about 30 psi of pressure. FIG. 46 illustrates an embodiment of the containment assembly 400 having a valve 506 in the hub 450. The valve 506 may be, for example, threaded into the hub 450. The syringe 480 may then be used to create a partial vacuum to remove air from the containment jacket 410. FIG. 46 illustrates a containment jacket 410 from which the air has been removed.

Figure 48:
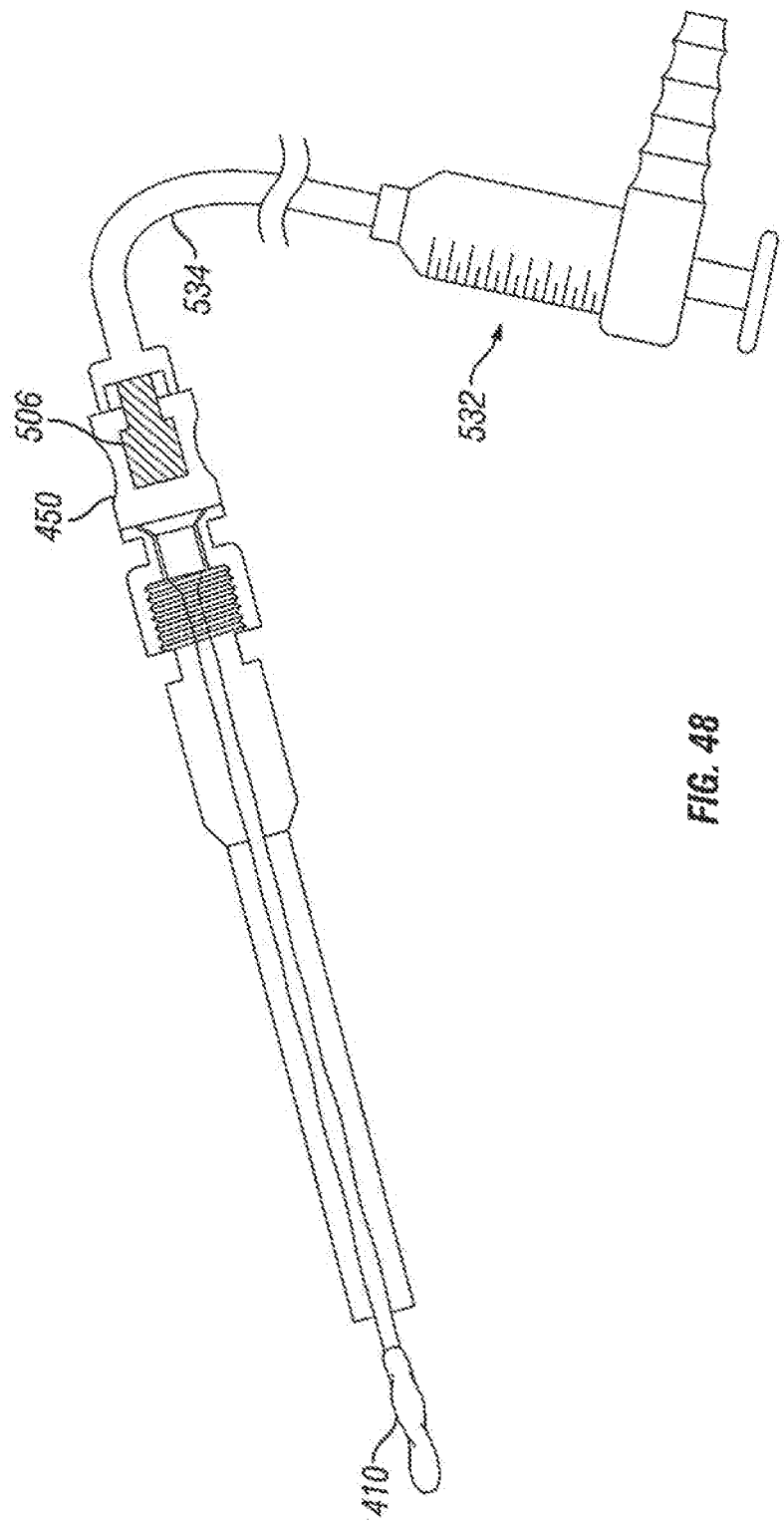
FIG. 48 illustrates use of a cement gun to introduce filler material into a containment jacket placed in a vertebral body in accordance with one embodiment of the present invention.
Figure 49:
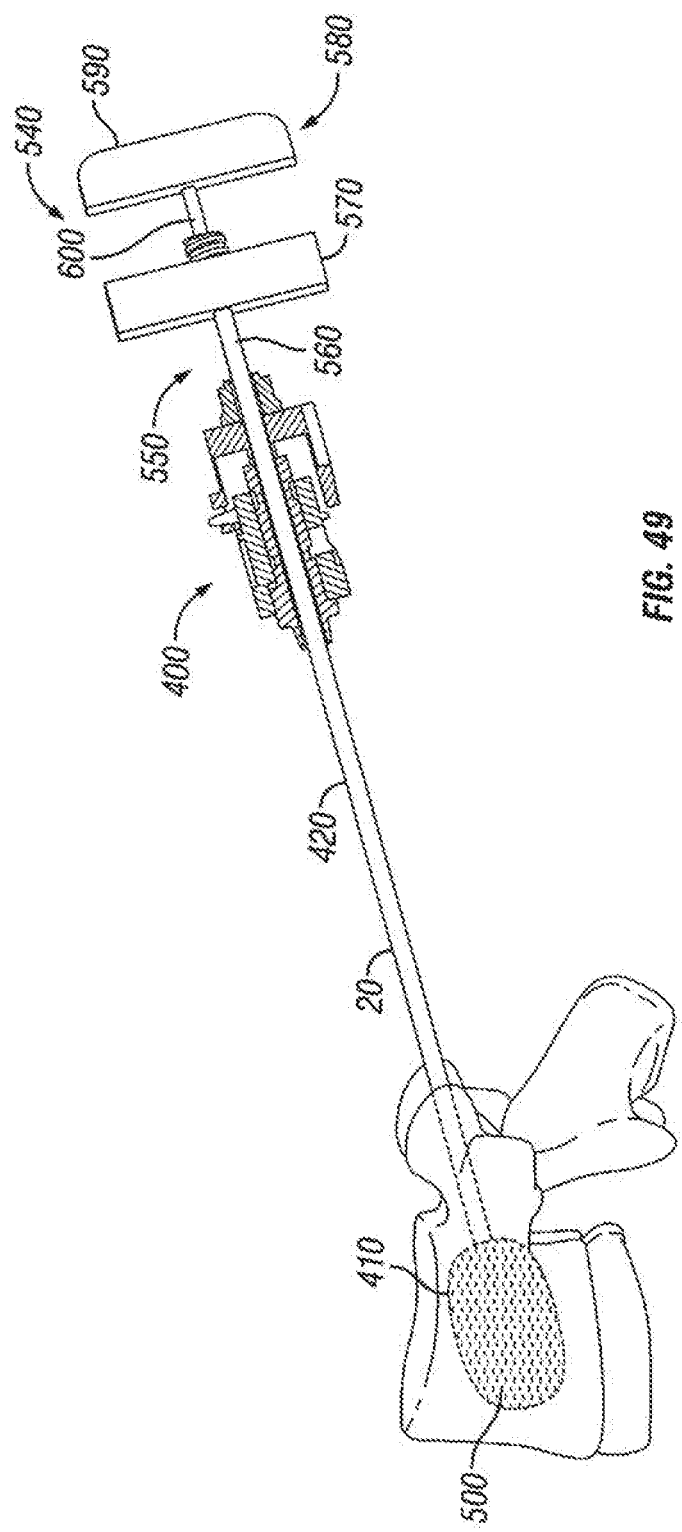
FIG. 49 illustrates use of a needle-type device to introduce filler material into a containment jacket placed in a vertebral body in accordance with one embodiment of the present invention.
Figure 50:
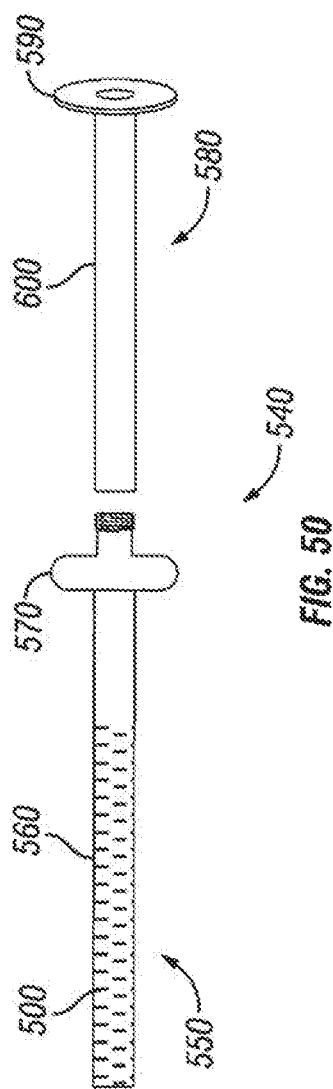

As previously mentioned, embodiments of the present invention may further include introduction of a filler material into the cavity 390. In an embodiment, the filler material may be introduced directly into the containment jacket 410 that has been placed within the cavity 390. FIGS. 47-49 illustrate procedures comprising introduction of a filler material 500 into the containment jacket 410 in accordance with embodiments of the present invention. In an alternative embodiment, a balloon assembly 280 may be used while introducing the filler material into the containment jacket 410. FIGS. 55-72 illustrate use of the balloon assembly 280 with the containment jacket 410 in accordance with one embodiment of the present invention.

FIG. 47 illustrates introduction of filler material 500 into the containment jacket 410 using a syringe-type device 510. As illustrated, plunger 520 of the syringe-type device 510 may be depressed to force filler material 500 from the body 530 of the syringe-type device 510, through the tubular member 420 of the containment assembly, and into the containment jacket 410. In an embodiment, introduction of the filler material 500 into the containment jacket 410 should expand the containment jacket 410. In some embodiments, the filler material 500 may be introduced into the containment jacket 410 until the containment jacket 410 at least partially fills the cavity 390 in the vertebral body 170. In some embodiments, the filler material 500 may be introduced at low pressure. In alternative embodiments, the filler material 500 should exert pressure to prevent (or reduce) loss of vertebral height. As illustrated, the containment jacket 410 may generally conform to the shape of the cavity 390. It may be desirable, in certain embodiments, for the containment jacket 410 to be a compliant balloon (e.g., polyurethane, collagen, silicone) that can contain the filler material 500 to prevent leakage. The containment jacket 410 may permit interdigitation of the filler material 500 with the cancellous bone 360 while being contained within the containment jacket 410.

While FIG. 47 illustrates use of syringe-type device 510 for introduction of the filler material 500, it should be understood that other suitable devices may be used to introduce the filler material 500 into the vertebral body 170. For example, FIG. 48 illustrates a cement gun 532 that can be used for the injection into the containment jacket 410. In the illustrated embodiment, extension tube 534 couples the cement gun 532 to the valve 506 in the hub 450. FIGS. 49-54 illustrate a needle-type device 540 that may be used to introduce the filler material 500. As illustrated, the body 550 of the needle-type device 540 comprises a hollow tube 560 having a through passageway and a stop 570 at one end. The needle-type device 540 further comprises a plunger 580 having a depression mechanism 590 and a needle 600 for insertion into the hollow tube 560. The length of the needle 600 may vary. For example, FIGS. 52 and 53 illustrate needles 600 that vary in length with the needle 600 of FIG.

52 longer in length. In an embodiment, the body 550 of the needle-type device 540 may be inserted into the tubular member 420 of the containment assembly 400. Plunger 580 may then be depressed to force the filler material 500 from the body 560 of the needle-type device 540 and into the containment jacket 410.

In addition to introducing the filler material 500 directly into the containment jacket 410 as illustrated by FIGS. 46-48, alternative embodiments of the present invention may utilize a balloon assembly 280 while introducing the filler material 500 into the containment jacket 410. The balloon assembly 280 may be used, for example, to maintain and/or restore vertebral height while introducing the filler material 500. FIGS. 55-72 and the accompanying description illustrate use of the balloon assembly 280 with the containment jacket 410 in accordance with one embodiment of the present invention.

Figure 55:
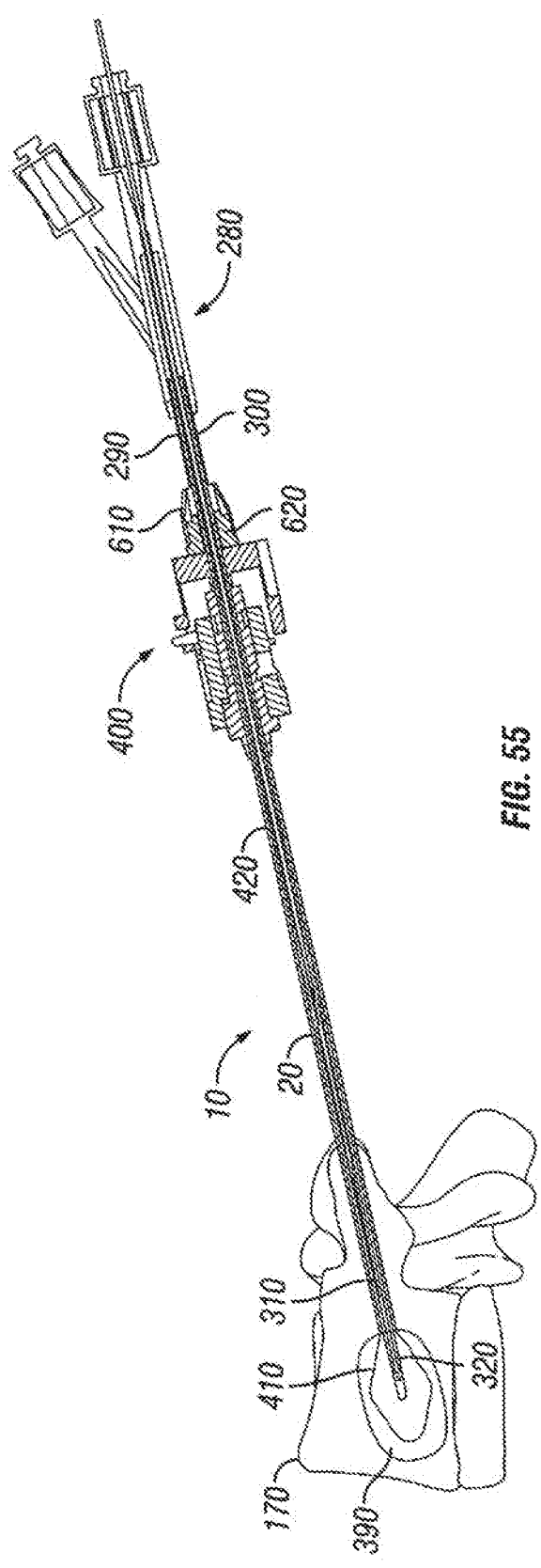
FIG. 55 illustrates insertion of a balloon into a containment jacket placed in a vertebral body in accordance with one embodiment of the present invention.
Figure 56:
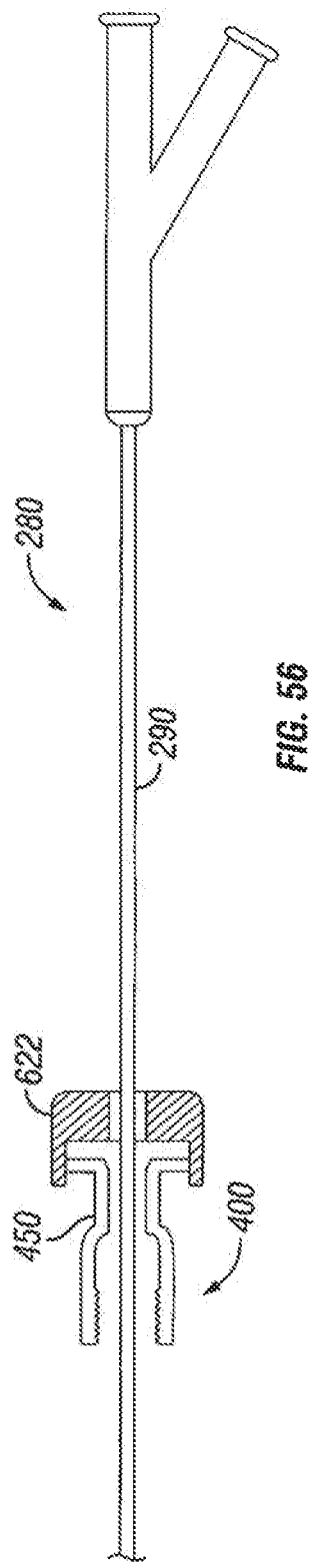
FIG. 56 illustrates coupling of the cannula assembly and the containment assembly in accordance with one embodiment of the present invention.

FIG. 55 illustrates insertion of balloon assembly 280 into the vertebral body 170 through the containment assembly 400 and the cannula assembly 10 in accordance with one embodiment of the present invention. As illustrated, cannula assembly 10 has been inserted into the vertebral body 170 with the cannula 20 providing access into the vertebral body 170. As further illustrated, the containment jacket 410 has already been inserted into the cavity 390. In an embodiment, the containment jacket 410 may be inserted by sliding the tubular member 440 with the containment jacket 410 disposed thereon through the cannula 20 of the cannula assembly 10. In accordance with embodiments of the present invention, the balloon assembly 280 may be inserted into vertebral body 170. As illustrated, the balloon assembly 280 includes a catheter 290 having a proximal end 300 and a distal end 310. A balloon 320 may be attached to the distal end 310 of the catheter 290.

As illustrated by FIG. 55, the balloon 320 may be inserted may be inserted into the containment jacket 410 through the tubular member 420 of the containment assembly 400. In an embodiment, the balloon 320 may be in a deflated stated when inserted through the tubular member 420. The balloon 320 may be inserted by sliding the catheter 290 with the balloon 320 disposed on the distal end 310 thereof through the tubular member 420 of the containment assembly 400. Once the balloon 320 has been placed, the balloon assembly 280 may be coupled to the containment assembly 400. By way of example, cap 610 disposed on the catheter 290 of the balloon assembly 280 may thread onto a luer fitting 620 on the hub 450 of the containment assembly 400. In an alternative embodiment, as illustrated by FIG. 55, the balloon assembly 280 may comprise luer cap 622. The luer cap 622 may be configured to freely spin on catheter 290 of the balloon assembly 280 (see, e.g., FIG. 55), in certain embodiments. In an embodiment, the luer cap 622 engages with the hub 450 of the containment assembly 400 to prevent movement of the balloon assembly 280 with respect to the containment assembly 400. In this manner, the balloon 320 can be precisely positioned within the vertebral body 170, for example.

After insertion of the balloon 320, fluid (e.g., air) may be removed from the containment jacket 410. The fluid may be removed, for example, in accordance with the previously discussed embodiments (e.g., FIGS. 45-46) for removal of fluid from the containment jacket 410. By way of example, a syringe may be used to remove air from within the containment jacket 410.

FIG. 57 illustrates inflation of balloon 320 after it has been inserted into the containment jacket 410 in accordance with one embodiment of the present invention. In general, inflation of the balloon 320 should provide pressure on the walls of the cavity 390 to prevent (or reduce) loss of vertebral height. It may be desirable, in certain embodiments, for expansion of the balloon 320 to further increase the height of the vertebral body 170. In certain embodiments, inflation of the balloon 320 may restore some vertebral height lost after the cavity 390 was initially created. As illustrated, the balloon 320 generally may be enclosed within the containment jacket 410. The volume of the balloon 320, when inflated, generally may be smaller than the volume of the containment jacket 410, in accordance with embodiments of the present invention. Furthermore, when inflated, the balloon 320 generally may not occupy the entire volume of the containment jacket 410. By way of example, the balloon 320 may occupy from about 25% to about 90% by volume of the containment jacket 410.

FIG. 58 illustrates introduction of filler material 500 into the containment jacket 410 in accordance with one embodiment of the present invention. As illustrated, the filler material 500 may be introduced into the containment jacket 410 through the inner lumen 340 of the inner catheter 330 of the balloon assembly 280. While not illustrated by FIG. 58, any of a variety of suitable devices may be used for introduction of the filler material including the devices illustrated by FIGS. 47-54. In general, the filler material 500 may be introduced into the portion of the containment jacket 410 that is not occupied by the balloon 320. In an embodiment, the filler material 500 may fill the portion of the containment jacket 410 that is not occupied by the balloon 320. The containment jacket 410 may expand with the introduction of the filler material 410. The filler material 500 may then be allowed to cure in the containment jacket 410. In an embodiment, the filler material 500 may exert pressure to prevent (or reduce) loss of vertebral height. It may be desirable, in certain embodiments, for the filler material 500 to exert pressure that further increases height of the vertebral body 170. As illustrated, the containment jacket 410 may generally conform to the shape of the cavity 390. It may be desirable, in certain embodiments, for the containment jacket 410 to a complaint balloon (e.g., polyurethane) that can contain the filler material 500 to prevent leakage while permitting interdigitation of the filler material 500 with the cancellous bone 360.

Filler material 500 generally comes into contact with the balloon 320 when the filler material 500 is introduced into the containment jacket 410 in accordance with embodiments of the present invention. For example, when the filler material 500 is introduced through the inner catheter 330 of the balloon assembly 280, the filler material 500 may accumulate, for example, on the distal face of the balloon 320. It should be understood that the balloon 320 may burst when it is under stress from inflation and comes into contact with the filler material 500.

Embodiments of the present invention may include a number of different techniques to reduce or potentially even prevent the potential bursting of the balloon 320 when the filler material 500 is introduced. For example, properties of the balloon 320 may be modified to increase its resistance to the filler material 500. In an embodiment, the shore hardness of the balloon 320 may be increased. For example, the shore hardness may be increased from a range of about 80 A to about 90 A to at least about 100 A (e.g., about 100 A to about 120 A). In another embodiment, the wall thickness of the balloon 320 may be increased. The wall thickness may be increased, for example from a range of about 0.1 mm to about 0.15 mm to a range of about 0.175 mm to about 0.2 mm. An additional technique may include applying a protective barrier (e.g., silicone, a hydrophobic material, Parylene poly(p-xylylene) polymers, etc). Another technique may include cross-linking the balloon material, for example, via gamma sterilization.

Additional techniques may include isolating the balloon 320 from the filler material 500 introduced into the containment jacket. FIGS. 59-63 illustrate an enclosure 632 disposed over the balloon 320 to prevent contact with the filler material 500 in accordance with one embodiment of the present invention. In an embodiment, the enclosure 632 may be fabricated with a material with high resistant to bone cement (e.g., polymethyl methacrylate). The material may also have a lower moisture vapor transmission rate, in certain embodiments. By way of example, the moisture vapor transmission rate may be less than about 1 g/100 in$^2$/day. As illustrated by FIG. 59, enclosure 632 may be placed over the balloon 320. As illustrated, the enclosure 632 may have a profile generally corresponding to the profile of the balloon 320. However, the enclosure 632 should generally be unstressed when the balloon 320 is inflated in accordance with certain embodiments. FIG. 60 illustrates an embodiment of the enclosure 632 having threads 636 holding the enclosure 632 in place over the balloon 320. In an embodiment, the threads 636 may be stitched to the balloon 320. FIGS. 61-63 illustrate alternate embodiments for placement of the enclosure 632 over the balloon 320. As illustrated by FIG. 61, the enclosure 632 may loosely fit over the balloon 320. As illustrated by FIG. 62, the nose 642 of the enclosure 632 may fit tightly over the nipple 638 of the balloon 320. As illustrated by FIG. 63, the nose 642 of the enclosure may be bonded to the nipple 638 of the balloon 320 with bonding agent 644.

Figure 64:
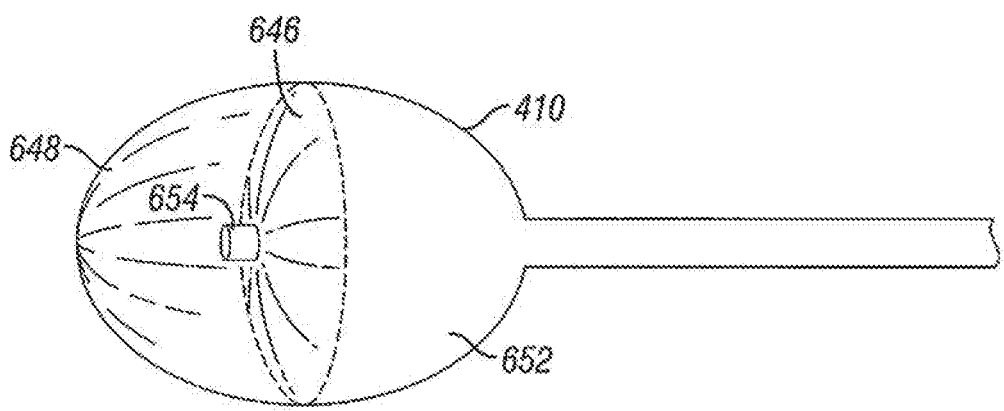
FIGS. 64-65 illustrate isolation of the balloon from the filler material in accordance with embodiments of the present invention.
Figure 65:
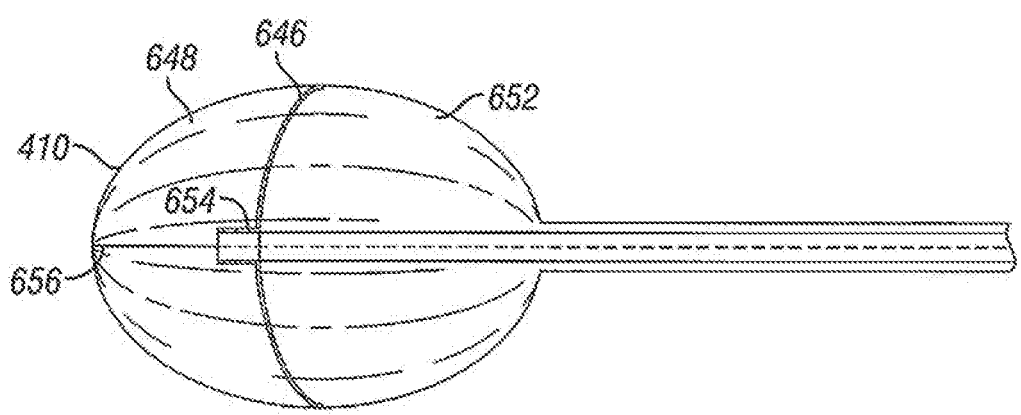

FIGS. 64-65 illustrate yet another technique for isolating the balloon 320 from the filler material 500 in accordance with one embodiment of the present invention. In the illustrated embodiment, the containment jacket 410 includes a dividing wall 646 that separates the containment jacket into a first section 648 and a second section 652. As illustrated, the dividing wall 646 may include an opening 654 for providing access to the first section 648 from the second section 652. In an embodiment (not illustrated), the balloon 320 may be inflated in the second section 652, and then the filler material 500 may be introduced into the first section 648. After removal of the balloon from the second section 652, an additional volume of the filler material 500 may be introduced into the second section 648. Alternatively, balloon 320 may first be inflated in the first section 648. In an embodiment, the balloon 320 may be threaded through the opening 654 and into the first section 648 over the guide wire 656 illustrated on FIG. 65.

Figure 66:
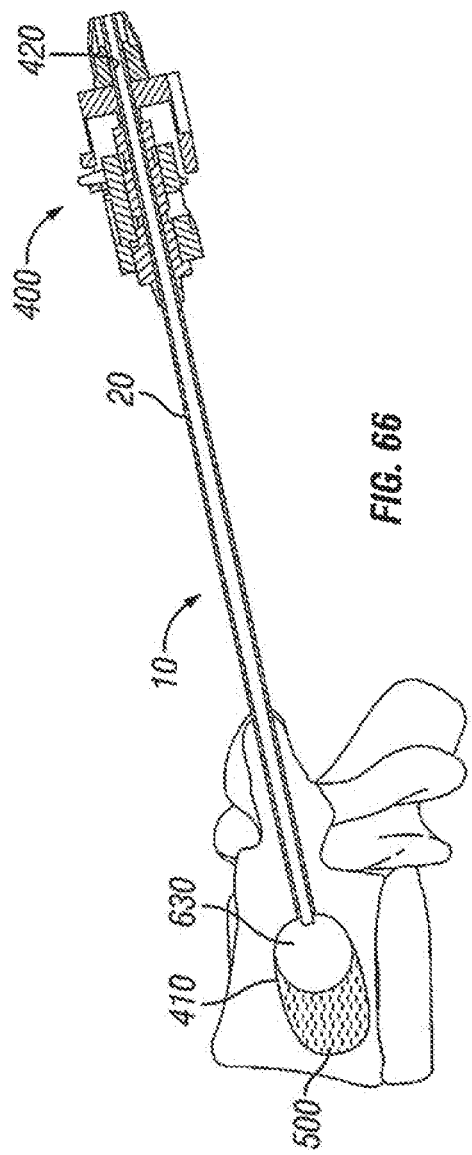
FIG. 66 illustrates a containment jacket placed within a vertebral body that has been partially filled in accordance with one embodiment of the present invention.

As illustrated by FIG. 66, after the filler material 500 has been allowed to cure, the balloon assembly 280 (e.g., shown on FIG. 58) may be removed. With removal of the balloon assembly 280 and, thus, the balloon 320 from within the containment jacket 410, a portion of the containment jacket 410 is not occupied. This unoccupied portion of the containment jacket is represented on FIG. 66 by reference number 630. As illustrated by FIG. 66, an access channel to the unoccupied portion 630 is maintained by tubular member 420 of the containment assembly 400 that is disposed within the cannula 20 of the cannula assembly 10.

Figure 67:
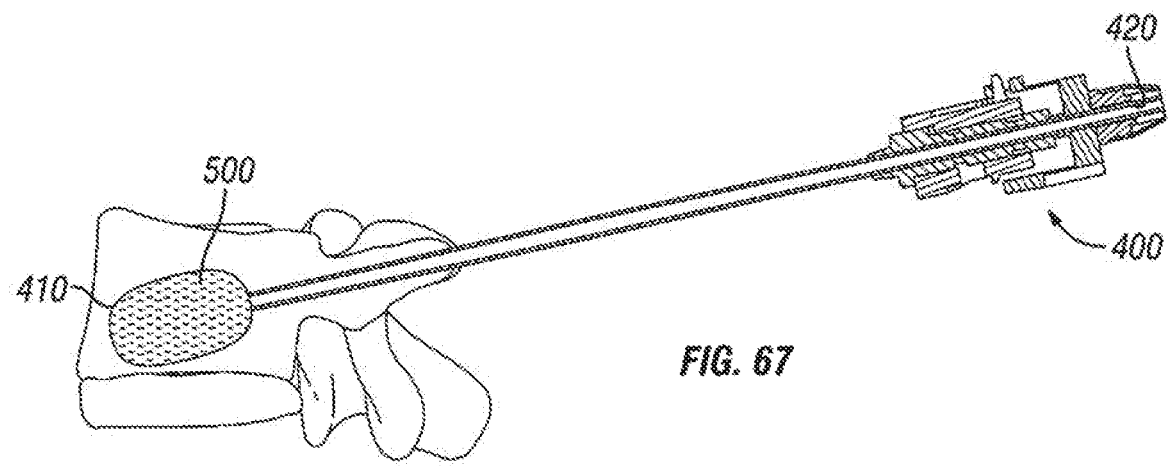
FIG. 67 illustrates introduction of filler material to fill the remainder of a containment jacket placed within a vertebral body in accordance with one embodiment of the present invention.

FIG. 67 illustrates introduction of an additional volume of the filler material 500 into the containment jacket 410. As illustrated, the additional volume of the filler material 500 may be introduced through the tubular member 420 of the containment assembly 400. The additional volume of the fill material may generally fill the unoccupied portion 630 (e.g., shown on FIG. 66) of the containment jacket 410 so that the containment jacket 410 is filled with the filler material 500, for example. While not illustrated by FIG. 67, any of a variety of suitable devices may be used for introduction of the additional volume of the filler material 500 including the devices illustrated by FIGS. 47-54. The additional volume of the filler material 500 may then be allowed to cure in the containment jacket 410.

Figure 68:
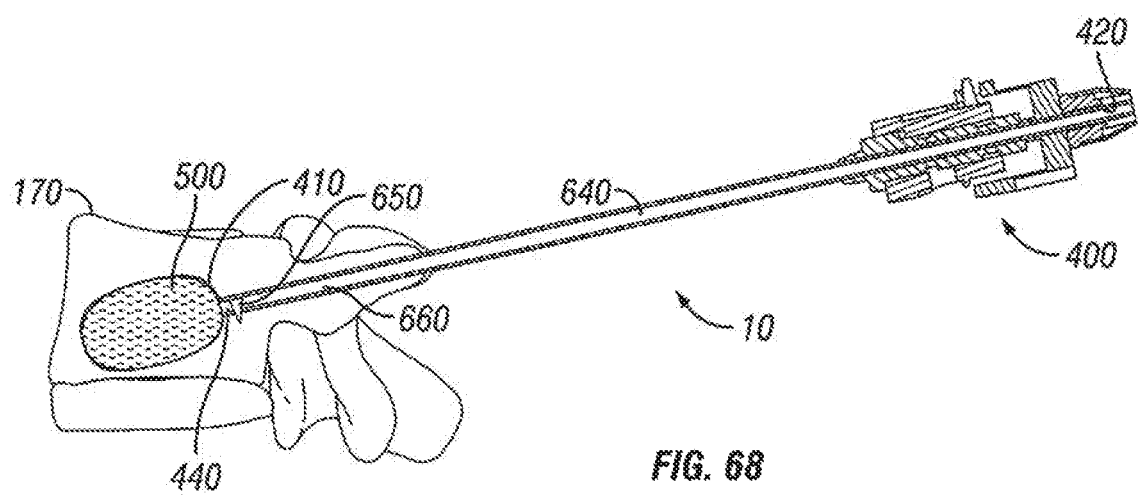
FIG. 68 illustrates detachment of the containment jacket from a containment assembly in accordance with one embodiment of the present invention.

Embodiments of the present invention further may include detaching the containment jacket 410 from the containment assembly 400. FIG. 68 illustrates removal of the containment jacket 410 in accordance with one embodiment of the present invention. As previously mentioned, the containment jacket 410 may be attached to the distal end 440 of the tubular member 420. As illustrated, a cutting device 640 having a cutting mechanism (e.g., cutting tips 650) in its distal end 660 may be inserted into the tubular member 420. In an embodiment, the cutting tips 650 include one or more blades. The cutting device 640 may then be used to detach the containment jacket 410, leaving the containment jacket 410 within the vertebral body 170. In another embodiment, the containment jacket 410 is provided with a perforated line detachment mechanism so that the containment jacket 410 can be detached and maintained within the vertebral body. Once the containment jacket 410 has been detached, the containment assembly 400 and the cannula assembly 10 may be removed, leaving the containment jacket 410. Accordingly, the containment jacket 410 containing the filler material 500 may be left within the vertebral body 170.

Figure 69:
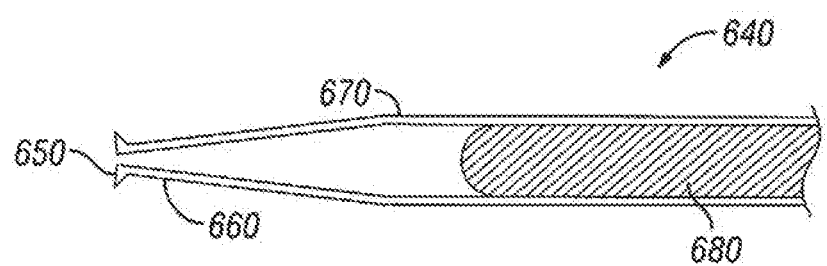
FIGS. 69-70 illustrate a cutting mechanism that can be used for detachment of the containment jacket in accordance with one embodiment of the present invention.
Figure 70:
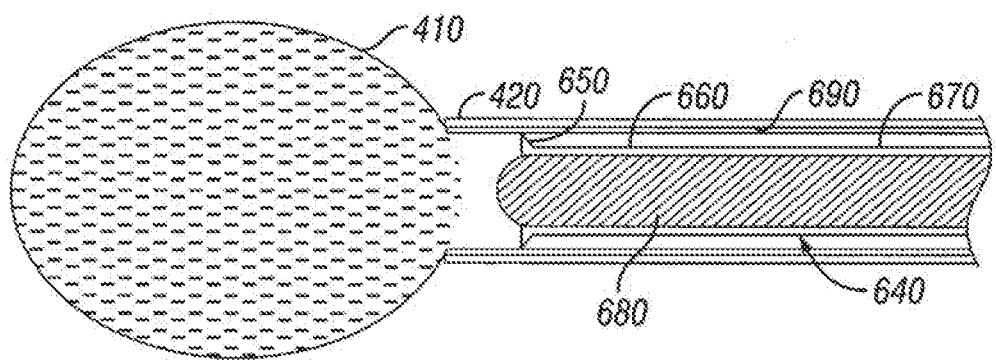

FIGS. 69-70 illustrate an embodiment of a cutting device 640 that may be used to detach the containment jacket 410. As illustrated, the cutting device 640 may include cutting tips 650 (e.g., blades) at its distal end 660. The cutting device 640 further includes outer tube 670 that narrows in diameter at the distal end 660. The cutting device 640 further includes plunger 680. In operation, the cutting device 640 may be inserted into the tubular member 420. The plunger 680 may be forced into the outer tube 670 forcing apart the cutting tips 650 into engagement with the containment jacket 410. The cutting device 640 may then be rotated (e.g., 360° rotation) to cut the containment jacket 410. In an embodiment, the internal face 690 of the tubular member 420 is used as backboard for cutting the containment jacket 410.

Figure 71:
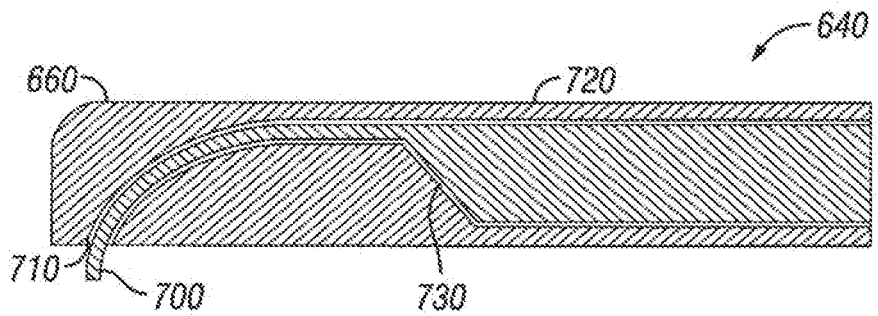
FIG. 71 illustrates a cutting mechanism that can be used for detachment of the containment jacket in accordance with another embodiment of the present invention.

FIG. 71 illustrates another embodiment of a cutting device 640 that may be used to detach the containment jacket 410. In the illustrated embodiment, the cutting device 640 includes cutting wire 700 that can be pushed out an opening 710 at the distal end 660 of the cutting device 640. The cutting wire 700 may have a rectangular or circular cross-sectional area, for example. While the cutting wire 700 is illustrated as extending from the opening 710 at a generally 90° angle, it should be understood that the cutting wire 700 may also extend at an angle of less than 90°. As illustrated, the cutting device 640 may include a main body 720 that includes internal cavity 730 with opening 710 at distal end 660. In operation, the cutting device 640 may be inserted into the tubular member 420 (e.g., shown on FIG. 70). The cutting wire 700 may then be pushed down to extend the cutting wire 700 from the opening 710 in the distal end 660 of the cutting device 640. The cutting wire 700 may engage the containment jacket 410 (e.g., shown on FIG. 70). The cutting device 640 may then be rotated (e.g., 360° rotation) to cut the containment jacket 410. It should be understood that the cutting device 640 illustrated in FIG. 71 may also be used for creation of the cavity 390 in the vertebral body 170. When used for cavity creation, the cutting wire 700 may extend from the opening 710 at an angle of less than 90° in certain embodiments.

While the preceding discussion describes the use of cutting device 640 to detach the containment jacket 410 from the containment assembly 400, it should be understood that other suitable techniques may be used for detachment. In an embodiment, the containment jacket 410 has perforations (not illustrated) on the neck wherein twisting the hub 450 of the containment assembly 400 detaches the containment jacket 410 at the perforations. Another embodiment may include a thread 484, as illustrated by FIG. 38, that secures the containment jacket 410 to the tubular member 420 of the containment assembly 400. As previously mentioned, a cord 486 may extend from the thread 484 that can be pulled to unravel the thread 484, detaching the containment jacket 410 from the tubular member 420.

Figure 72:
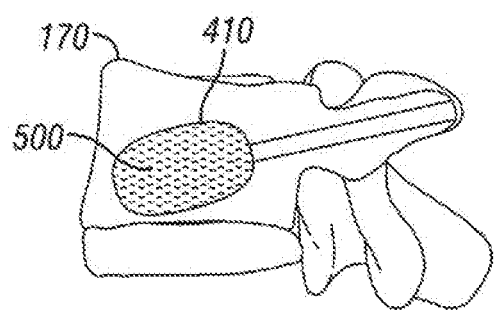
FIG. 72 illustrates a containment jacket placed within a vertebral body, the containment jacket containing a filler material, in accordance with one embodiment of the present invention.

FIG. 72 illustrates a containment jacket 410 within a vertebral body 170 and containing a filler material 500 in accordance with one embodiment of the present invention. In an embodiment (FIGS. 47-49), the filler material 500 may be introduced directly into the containment jacket 410. In an alternative embodiment (FIGS. 55-72), a balloon assembly 280 may be used while introducing the filler material 500 into the containment jacket 410. In an embodiment, the filler material 500 may be introduced at low pressure. In an alternative embodiment, the filler material 500 may exert pressure to prevent (or reduce) loss of vertebral height.

The preceding description describes the use of a filler material 500 in accordance with embodiments of the present invention. Those of ordinary skill in the art will appreciate that the filler material 500 may comprise any of a variety of materials that may be utilized to, for example, fill and stabilize the cavity 390 in the vertebral body 170. Examples of suitable materials may include bone cements (e.g. polymethyl methacrylate), human bone graft and synthetic derived bone substitutes.

In addition, the preceding description is directed, for example, to treatment of vertebral fractures that includes a containment assembly for cement containment and/or a balloon assembly for maintaining vertebral height. It should be understood that the present technique also may be used in other suitable bone treatments were maintenance of vertebral height and/or cement containment may be desired. By way of example, embodiments of the present invention may be used to treat tibia plateau fractures, distal radius fractures, and cancellous fractures.

While it is apparent that the invention disclosed herein is well calculated to fulfill the objects stated above, it will be appreciated that numerous modifications and embodiments may be devised by those skilled in the art.

What is claimed is:

1. A surgical method comprising:
creating a cavity in bone by inserting a cutting device into the bone; and
introducing filler material into the cavity,
wherein the cutting device comprises an outer tube having a slot formed in a side of the outer tube, a connecting rod extending through the outer tube, a cutting mechanism connected to a distal end of the connecting rod, and a handle assembly,
wherein the cutting mechanism includes a first blade coupled to the connecting rod via a first hinge, a second blade coupled to a distal end of the outer tube via a second hinge and to the first blade via a third hinge, wherein the cutting mechanism is moveable between a first position in which the cutting mechanism is entirely disposed within the outer tube and a second position in which the cutting mechanism extends through the slot of the outer tube, and wherein in the second position, the first blade overlaps with the second blade.

2. The surgical method of claim 1, wherein the handle assembly is connected to the outer tube.

3. The surgical method of claim 2, wherein the handle assembly comprises a handle ball.

4. The surgical method of claim 3, wherein the handle ball is threaded onto the connecting rod.

5. The surgical method of claim 1, further comprising inserting a containment assembly into the cavity prior to introducing filler material into the cavity.

6. The surgical method of claim 5, wherein the containment assembly comprises a containment jacket and a tubular member, wherein the containment jacket is disposed on a distal end of the tubular member.

7. The surgical method of claim 6, wherein the containment jacket comprises a neck placed over a distal tip of the tubular member.

8. A surgical method comprising:
creating a cavity in bone by inserting (i) a balloon and (ii) a cutting device into the bone; and
introducing filler material into the cavity,
wherein the cutting device comprises an outer tube having a slot formed in a side of the outer tube, a connecting rod extending through the outer tube, a cutting mechanism connected to a distal end of the connecting rod, and a handle assembly,
wherein the cutting mechanism includes a first blade coupled to the connecting rod via a first hinge, a second blade coupled to a distal end of the outer tube via a second hinge and to the first blade via a third hinge, wherein the cutting mechanism is moveable between a first position in which the cutting mechanism is entirely disposed within the outer tube and a second position in which the cutting mechanism extends through the slot of the outer tube, and wherein in the second position, the first blade overlaps with the second blade.

9. The surgical method of claim 8, wherein the handle assembly is connected to the outer tube.

10. The surgical method of claim 9, wherein the handle assembly comprises a handle ball.

11. The surgical method of claim 10, wherein the handle ball is threaded onto the connecting rod.

12. The surgical method of claim 8, further comprising inserting a containment assembly into the cavity prior to introducing filler material into the cavity.

13. The surgical method of claim 12, wherein the containment assembly comprises a containment jacket and a tubular member, wherein the containment jacket is disposed on a distal end of the tubular member.

14. The surgical method of claim 13, wherein the containment jacket comprises a neck placed over a distal tip of the tubular member.

* * * * *